(12) United States Patent
Convit

(10) Patent No.: US 12,036,188 B2
(45) Date of Patent: *Jul. 16, 2024

(54) IMMUNOGENIC COMPOSITION FOR THE TREATMENT OF CANCER AND METHODS OF PREPARING THE SAME

(71) Applicants: Jacinto Convit World Organization Inc., Pompano Beach, FL (US); Fundacion Jacinto Convit, Caracas (VE)

(72) Inventor: Jacinto Convit, Caracas (VE)

(73) Assignees: JACINTO CONVIT WORLD ORGANIZATION INC., Pompano Beach, FL (US); FUNDACION JACINTO CONVIT, Caracas (VE)

(*) Notice: Subject to any disclaimer, the term of this patent is extended or adjusted under 35 U.S.C. 154(b) by 259 days.

This patent is subject to a terminal disclaimer.

(21) Appl. No.: 17/460,979

(22) Filed: Aug. 30, 2021

(65) Prior Publication Data

US 2021/0386687 A1 Dec. 16, 2021

Related U.S. Application Data

(63) Continuation of application No. 16/099,970, filed as application No. PCT/US2017/031997 on May 10, 2017, now Pat. No. 11,103,466.

(30) Foreign Application Priority Data

May 10, 2016 (VE) .............................. 2016-000212

(51) Int. Cl.
*A61K 31/115* (2006.01)
*A61K 39/00* (2006.01)
*A61P 35/00* (2006.01)

(52) U.S. Cl.
CPC ........ *A61K 31/115* (2013.01); *A61K 39/0011* (2013.01); *A61P 35/00* (2018.01); *A61K 2039/55594* (2013.01)

(58) Field of Classification Search
None
See application file for complete search history.

(56) References Cited

U.S. PATENT DOCUMENTS

| | | | |
|---|---|---|---|
| 11,103,466 B2 * | 8/2021 | Convit | A61K 39/0011 |
| 2005/0106155 A1 | 3/2005 | Ohno et al. | |
| 2006/0148064 A1 | 6/2006 | Srivastava | |

FOREIGN PATENT DOCUMENTS

| | | |
|---|---|---|
| EP | 0915708 B1 | 10/2008 |
| WO | 2013111084 A1 | 8/2013 |

OTHER PUBLICATIONS

Cho, Ki Yun; International Search Report and Written Opinion for PCT/US2017/031997 as mailed Aug. 8, 2017; 16 pages.
Convit, J., et al.; "Autologous tumor lysate/Bacillus Calmette-Guerin immunotherapy as an adjuvant to conventional breast cancer therapy"; Clinical and Translational Oncology, vol. 17, No. 11; Jun. 16, 2015; pp. 884-887.
Yuan, Shifang, et al.; "A Novel Bacillus Calmette-Guerin-based Breast Cancer Vaccine that Coexpresses Multiple Tandem Repeats of MUC1 and CD80 Breaks the Immune Tolerance and Inhibits MUC1-Positive Breast Cancer Growlh"; Cancer Biotherapy and Radiopharmaceuticals, vol. 24, No. 5; Oct. 2009; pp. 607-613.
Feldman, John P., et al.; "A Mathematical Model for Tumor Volume Evaluation using Two-Dimensions"; Journal of Applied Quantitative Methods, vol. 4, No. 4; Nov. 2008; pp. 455-462.
Mihara, H., et al.; "Transient receptor potential vanilloid 4 {TRPV4)-dependent calcium influx and ATP release in mouse oesophageal keratinocytes"; The Journal of Physiology, vol. 589, No. 14; May 3, 2011; pp. 3471-3482.
Ahn, Andrew H., et al.; "Tissue Injury Regulates Serotonin 1D Receptor Expression: Implications for the Control of Migraine and Inflammatory Pain"; The Journal of Neuroscience, vol. 26, No. 32; Aug. 9, 2006; 18 pages.
Ysebaert, Dirk K., et al.; "Identification and kinetics of leukocytes after severe ischaemia/reperfusion renal injury"; Nephrology Dialysis Transplantation, vol. 15, No. 10; Oct. 2000; pp. 1562-1574.
Kim, Seong Min, et al.; "Effect of selective cyclooxygenase-2 inhibitor meloxicam on liver fibrosis in rats with ligated common bile ducts"; Hepatology Research, vol. 38, No. 8; Jul. 8, 2008; pp. 800-809.
Pirog, Edyta Catalina, et al.; "Diagnostic and Prognostic Significance of the Mitotic Index in Endometrial Adenocarcinoma"; Gynecologic Oncology, vol. 46, No. 3; Sep. 1992; pp. 337-340.
Tzekov, Radouil, et al.; "Repetitive Mild Traumatic Brain Injury Causes Optic Nerve and Retinal Damage in a Mouse Model"; Journal of Neuropathology and Experimental Neurology, vol. 73, No. 4; Apr. 2014; pp. 345-361.

(Continued)

*Primary Examiner* — Yunsoo Kim
(74) *Attorney, Agent, or Firm* — BAKER & MCKENZIE LLP; Steven A. Rogers

(57) ABSTRACT

The present disclosure relates, in some embodiments, to an immunogenic compositions for the treatment of cancer, methods of preparing an immunogenic composition for the treatment of cancer, and methods of treating cancer subjects with an immunogenic composition.

Some embodiments of the present disclosure relate to an immunogenic composition operable as a treatment of cancer in a subject having a subject weight, the immunogenic composition including: an immunoactive tissue extract comprising a protein composition, wherein the immunogenic composition has a final concentration of the protein composition of about 6 mg to about 10 mg of the protein composition per kg of the subject weight; an immune response activator comprising a BCG solution, wherein the immunogenic composition has a final concentration of the immune response activator of about 0.525 to about 0.725 mg of the BCG solution per mL of the immunogenic composition; and an immune response mitigator comprising a formaldehyde solution, wherein the immunogenic composition has a final concentration of the formaldehyde solution of about 0.005% to about 0.035%.

20 Claims, 19 Drawing Sheets

(56) References Cited

OTHER PUBLICATIONS

Moffitt, Phil; "A methyl green-pyronin technique for demonstrating cell death in the murine tumour S180"; Cell Biol Int. vol. 18, No. 6; Jun. 1994; pp. 677-679.
Mote, R.F., et al.; "A Staining Method Using Acridine Orange and Auramine O for Fungi and Mycobacteria in Bovine Tissue"; Stain Technology, vol. 50, No. 1; Jan. 1975; pp. 5-9.
Webster et al.; "Effects of prolonged formalin fixation on diagnostic immunohistochemistry in domestic animals"; Journal of Histochemistry and Cytochemistry, vol. 57, No. 8; Aug. 2009; pp. 753-761.
Kruger, The protein Protocol Handbook, 3rd Ed., p. 17-24 (Year: 2009).

* cited by examiner

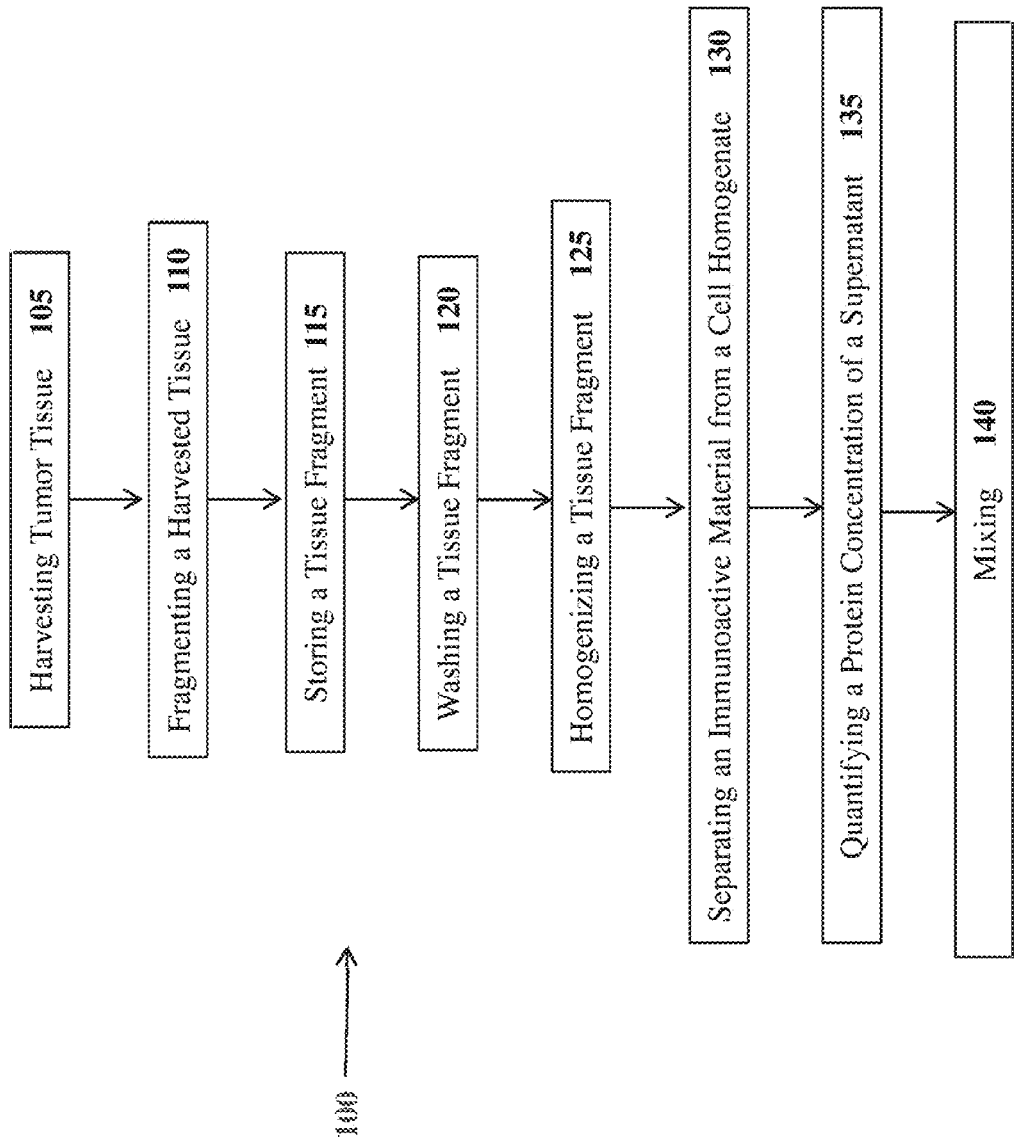

IMMUNOGENIC COMPOSITION FOR THE TREATMENT OF CANCER AND METHODS OF PREPARING THE SAME

CROSS-REFERENCE TO RELATED APPLICATIONS

This U.S. patent application claims priority to and is a continuation patent application of U.S. patent application Ser. No. 16/099,970 filed on Nov. 8, 2018 which is a 371 application of PCT/US2017/031997 filed on May 10, 2017, which claims priority to Venezuelan Application No. 2016-000212 filed May 10, 2016, the contents of which are hereby incorporated in their entirety by reference.

FIELD OF THE DISCLOSURE

The present disclosure relates, in some embodiments, to an immunogenic composition that may be used in the immunotherapeutic treatment of cancer (e.g., breast cancer). Further, the present disclosure relates to methods of producing an immunogenic composition that may be used in the immunotherapeutic treatment of cancer (e.g., breast cancer). Moreover, the present disclosure relates to the immunotherapeutic treatment of a cancer subject (e.g., a breast cancer subject) using an immunogenic composition.

BACKGROUND OF THE DISCLOSURE

Nearly 1 in 6 deaths are the result of cancer, making cancer the second most common cause of death globally. In 2015 alone cancer was responsible for 8.8 million deaths, with 70% of these deaths occurring in low or middle-income countries.

Despite improvements in diagnosis and care, globally breast cancer remains the second most common cancer and the most common cancer among women. In 2012, approximately twenty-five percent of all cancers diagnosed were breast cancer, an estimated 1.67 million cases. Breast cancer was the fifth most common cause of cancer deaths in 2012, claiming the lives of 522,000 patients. In less developed regions of the world, breast cancer is the most common cause of cancer deaths amongst women, approximately 14%. Moreover, breast cancer is the second most common cause of cancer death amongst all patients, with only lung cancer claiming more lives in 2012. It is estimated that almost a quarter of a million people will be diagnosed with invasive breast cancer and about 40,000 deaths in the United States alone in 2016.

Moreover, between 5 and 45% of breast cancer patients suffer local relapse or metastasis following surgery. Multiple factors may contribute to the rate of relapse including depression of cell-mediated immunity through cancer growth, chemotherapy, and/or radiation treatment regimes.

However, immunotherapeutic treatments for the treatment of breast cancer and reduction of relapse have been encumbered by inadequate preparative methods resulting in compounds that lack desirable immunoactivity.

SUMMARY

Accordingly, a need has arisen for improved immunogenic compositions that may be used in the treatment of cancer (e.g., breast cancer, colorectal, lung) and methods for preparing such immunogenic compositions.

The present disclosure relates, according to some embodiments, to an immunogenic composition operable for the treatment of cancer, methods of preparing an immunogenic composition for the treatment of cancer, and methods of treating cancer subjects with an immunogenic composition.

Some embodiments of the present disclosure relate to an immunogenic composition operable as a treatment of cancer (e.g., a breast cancer) in a subject having a subject weight, the immunogenic composition including: an immunoactive tissue extract comprising a protein composition; an immune response activator comprising a BCG solution (e.g., a live attenuated Danish strain 1331); and an immune response mitigator comprising a formaldehyde solution. In some embodiments, an immunogenic composition may have a final concentration of a protein composition of about 6 mg to about 10 mg of the protein composition per kg of a subject weight. An immunogenic composition, in some embodiments may have a final concentration of a protein composition of about 8 mg of the protein composition per kg of a subject weight. An immunogenic composition, according to some embodiments, may have a final concentration of an immune response activator of about 0.525 to about 0.725 mg of the BCG solution per mL of the immunogenic composition. In some embodiments a final concentration of an immune response activator may be about 0.625 mg of a BCG solution per mL of the immunogenic composition. According to some embodiments, an immunogenic composition may have a final concentration of a formaldehyde solution of about 0.005% to about 0.035%. In some embodiments, an immunogenic composition may have a final concentration of a formaldehyde solution of about 0.02%.

Some embodiments of the present disclosure relate to a method of preparing an immunogenic composition operable as a treatment of cancer for a subject having a subject weight, the method including: homogenizing a tissue fragment in a suspension solution to form a cell homogenate, wherein the tissue fragment comprises neoplastic breast tissue from the subject or is autologous to neoplastic breast tissue from the subject; separating (e.g., centrifugation) the cell homogenate to form a supernatant and a precipitate, wherein the supernatant comprises a protein composition comprising an immunoactive material; quantifying the protein composition (e.g., Bradford assay); and mixing a volume of the supernatant with a BCG solution and a formaldehyde solution to generate the immunogenic composition. According to some embodiments, an immunogenic composition may have a final concentration of about 6 mg to about 10 mg of a protein composition per kg of the subject weight, about 0.525 to about 0.725 mg of a BCG solution per mL of the immunogenic composition, and about 0.005% to about 0.035% of a formaldehyde solution per volume of the immunogenic composition. In some embodiments, homogenizing a tissue fragment in a suspension solution may be performed at a ratio of about 0.5 g of the tissue fragment per about 1 mL of the suspension solution. In some embodiments, a suspension solution may be PBS. According to some embodiments, a BCG solution may be a live attenuated Danish strain 1331.

According to some embodiments, a method of preparing an immunogenic composition may further include: harvesting a tumor tissue from a subject or from a tissue culture derived from a neoplastic breast tissue sample obtained from the subject to form a harvested tissue; and fragmenting the harvested tissue to form the tissue fragment. A method, in some embodiments, may further include combining a tissue fragment with a storage solution (e.g., PBS plus antibiotic), and storing the tissue fragment at a temperature of $\leq -80°$ C.

In some embodiments, a method of preparing an immunogenic composition may include washing the tissue fragment in a wash solution of PBS and at least one antibiotic or antifungal. According to some embodiments, homogenizing a tissue fragment may include pulverizing the tissue sample using at least 10 strokes of a glass homogenizer. Separating a cell homogenate to form a supernatant and a precipitate, according to some embodiments, may include centrifugation, for example, centrifugation at a relative centrifugal force of 250 g for 10 minutes.

The present disclosure relates, in some embodiments, to a method of treating a cancer subject with an immunogenic composition, the method including: (a) homogenizing a tissue fragment in a suspension solution to form a cell homogenate, wherein the tissue fragment may be neoplastic tissue from the cancer subject or may be autologous to neoplastic breast tissue from the cancer subject; (b) separating the cell homogenate to form a supernatant and a precipitate, wherein the supernatant includes a protein composition comprising an immunoactive material; (c) quantifying the protein composition; (d) mixing a volume of the supernatant with a BCG solution and a formaldehyde solution to generate the immunogenic composition, wherein the immunogenic composition has a final concentration comprising: about 6 mg to about 10 mg of the protein composition per kg of the subject weight, about 0.525 to about 0.725 mg of the BCG solution per mL of the immunogenic composition, and about 0.005% to about 0.035% of the formaldehyde solution per volume of the immunogenic composition; and (e) injecting the immunogenic composition intradermally into a deltoid region of the cancer subject. According to some embodiments, homogenizing a tissue fragment in a suspension solution may be performed at a ratio of about 0.5 g of the tissue fragment per about 1 mL of the suspension solution. In some embodiments, a method may include repeating steps (a) through (e) every six weeks for at least 18 weeks.

BRIEF DESCRIPTION OF THE DRAWINGS

Some embodiments of the disclosure may be understood by referring, in part, to the present disclosure and the accompanying drawings, wherein:

FIG. 1 illustrates a flow diagram of a generalized workflow for preparing an immunogenic composition, according to a specific example embodiment of the disclosure.

DETAILED DESCRIPTION

Figure 2B:
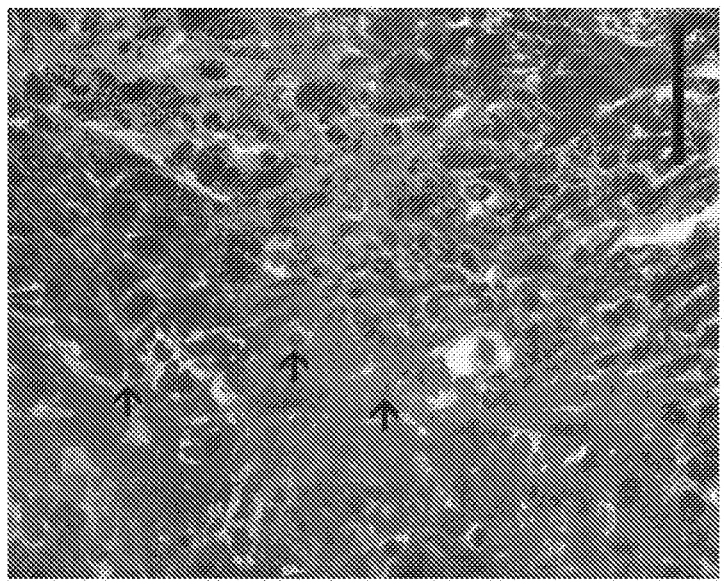
FIG. 2B illustrates microscopic imaging of zone 2 harvested from a G1 treatment mouse, according to a specific example embodiment of the disclosure.

An Immunogenic Composition for the Treatment of Cancer

The present disclosure relates, in some embodiments, to immunogenic compositions, for example, immunogenic compositions that may be used as a treatment of cancer (e.g., breast cancer, colorectal) in a subject (e.g., a human subject, a mouse subject). According to some embodiments, an immunogenic composition may be used in the treatment of breast cancer. In some embodiments, an immunogenic composition may be used in the treatment of one or more cancers, including for example lung, colorectum, prostate, stomach, liver, cervical, esophageal, bladder, pancreatic, kidney, ovarian, testicular, and skin cancers.

According to some embodiments, an immunogenic composition operable as a treatment of cancer (e.g., breast cancer) in a patient may include: an immunoactive tissue extract comprising an immunoactive material; an immune response activator (e.g., a BCG vaccine); and an immune response mitigator (e.g., formalin).

An immunogenic composition may comprise, in some embodiments, at least one immunoactive material (e.g., a tumor associated antigen (TAA)). In some embodiments, an immunoactive material may be operable to trigger an immune response in a patient specific to a cancerous tissue (e.g., neoplastic breast tissue, tumor tissue). An immunoactive material may comprise a length of peptide-bonded amino acids (e.g., peptide, polypeptide, protein), a carbohydrate, a lipid, a nucleic acid, multiples thereof, or any combinations thereof. According to some embodiments, an immunoactive material may comprise one or more antigens (e.g., a TAA). According to some embodiments, an immunoactive material may include one or more antigens derived from a tumor at any stage of development. For example, an immunoactive material may be derived from a tumor tissue harvested at any stage of tumor development. In some embodiments, a stage of tumor development at which a tumor tissue is harvested and an immunoactive material derived therefrom may be selected based on a quantity of different antigens present in the tumor tissue during the stage of development, an abundance of a selected antigen in the tumor tissue during the stage of development, or both.

An immunoactive tissue extract, according to some embodiments, may include an immunoactive material. An immunoactive tissue extract, in some embodiments, may be derived from a tumor sample (e.g., neoplastic breast tissue) obtained from a patient or autologous to a patient (e.g., produced in a tissue culture). According to some embodiments, an immunoactive tissue sample may be a homogenized tumor sample (e.g., neoplastic breast tissue). There are many methods by which a tumor sample may undergo homogenization. According to some embodiments, homogenization of a tumor sample may include cutting, slicing, fragmenting, mincing, pulverizing, blending, grinding, or any combination thereof. Homogenization of a tumor sample may include using a glass homogenizer, in some embodiments. In some embodiments, homogenization of a tumor sample may include pulverizing the tumor sample using at least 8 strokes, or at least 10 strokes, or at least 12 strokes, or at least 14 strokes, or at least 16 strokes, or at least 18 strokes, or at least 20 strokes of a glass homogenizer.

In some embodiments, an immunoactive tissue extract may be or arise from a tumor tissue sample subjected to separation, isolation, purification, or any combination thereof such that at least a portion of the immunoactive material may be separated from the tumor sample (e.g., neoplastic breast tissue). For example, in some embodiments, an immunoactive material may be taken or derived from a tumor sample by separation of a homogenized tumor sample into a supernatant and a precipitate, where the immunoactive material is present in the supernatant. Separation of a homogenized tumor sample, in some embodiments, may include centrifugation, filtration, or any combination thereof. A supernatant may include a supernatant protein concentration comprising an immunoactive material, according to some embodiments. A supernatant protein concentration may be quantified, for example using a Bradford Assay.

According to some embodiments, an immunogenic composition may include a supernatant protein (e.g., an immunoactive material) at a concentration relative to a total weight of a subject. In some embodiments, a supernatant protein may optionally arise from an immunoactive tissue extract. An immunogenic composition may include a supernatant protein (e.g., an immunoactive material) at any concentration relative to a subject's total weight. In some embodiments, an immunogenic composition may include a supernatant protein at a concentration of 6 mg per kg of a subject's weight (mg/kg), or 7 mg/kg, or 8 mg/kg, or 9 mg/kg, or 10 mg/kg, in some embodiments. In some embodiments, an immunogenic composition may include a supernatant protein at a concentration of about 6 mg of the supernatant protein per kg of a subject's weight (mg/kg), or about 7 mg/kg, or about 8 mg/kg, or about 9 mg/kg, or about 10 mg/kg, where about represents plus or minus 10%. An immunogenic composition, according to some embodiments, may include a supernatant protein at a concentration of about 6 mg of the supernatant protein per kg of a subject's weight (mg/kg) to about 10 mg/kg, or about 7 mg/kg to about 9 mg/kg, or about 8 mg/kg to about 10 mg/kg, or about 9 mg/kg to about 10 mg/kg, where about represents plus or minus 10%.

In some embodiments, an immunogenic composition may include an immune response activator. An immune response activator (e.g., a BCG vaccine), in some embodiments, may be operable to activate a subject's immune system triggering a Th1 immune response (e.g., targeted to a subject's tumor cells).

An immune response activator, in some embodiments, may include a *Bacillus* Calmette-Guerin (BCG) vaccine (e.g., a BCG solution). According to some embodiments, a BCG vaccine may include a live attenuated Danish strain 1331 (Staten Serum Institute, Copenhagen), BCG Connaught (Sanofi Pasteur), BCG Glaxo (ATCC #35741), BCG Japanese (ATC #35737), BCG Pasteur (ATCC #35734), BCG Tice (Merck), or any combination thereof. An immunogenic composition may include a concentration of a BCG vaccine (e.g., Danish strain 1331) of 0.525 mg of BCG per mL of immunogenic composition (mg/mL), or 0.550 mg/mL, or 0.575 mg/mL, or 0.60 mg/mL, 0.625 mg/mL, or 0.650 mg/mL, or 0.675 mg/mL, or 0.70 mg/mL, or 0.725 mg/mL, according to some embodiments. In some embodiments, an immunogenic composition may include a concentration of a BCG vaccine (e.g., Danish strain 1331) of about 0.525 mg of BCG per mL of immunogenic composition (mg/mL), or about 0.550 mg/mL, or about 0.575 mg/mL, or about 0.60 mg/mL, about 0.625 mg/mL, or about 0.650 mg/mL, or about 0.675 mg/mL, or about 0.70 mg/mL, or about 0.725 mg/mL, where about represents plus or minus 10%. According to some embodiments, an immunogenic composition may include a concentration of a BCG vaccine (e.g., Danish strain 1331) of about 0.525 mg of BCG per mL of immunogenic composition (mg/mL) to about 0.725 mg/mL, or about 0.550 mg/mL to about 0.725 mg/mL, or about 0.575 mg/mL to about 0.70 mg/mL, or about 0.60 mg/mL to about 0.675 mg/mL, or about 0.625 mg/mL to about 0.675 mg/mL, or about 0.60 mg/mL to about 0.65 mg/mL where about represents plus or minus 10%.

An immune response activator, in some embodiments, may include an adjuvant. An adjuvant may comprise a single activator or a combination of activators selected from a group comprising cytokines, alum, aluminum hydroxide, aluminum phosphate, calcium phosphate hydroxide, paraffin oil, squalene, detergents, saponins, adjuvant 65, Freund's complete adjuvant, Freud's incomplete adjuvant, killed bacterial products, attenuated bacterial products, or any other desirable adjuvant.

In some embodiments, an immunogenic composition may include an immune response mitigator (e.g., formalin, formaldehyde). An immune response mitigator may be operable to mitigate an immune response (e.g., induced by an immune response activator) thereby preventing an exacerbated immune response while retaining an immunogenic composition's ability to stimulate an antigen response (e.g., targeted to tumor tissue).

An immune response mitigator, according to some embodiments may include a formalin solution or a formaldehyde solution. The terms formalin and formaldehyde solution are used interchangeably throughout this specification and refer to a liquid form of formaldehyde. According to some embodiments, an immunogenic composition may have a concentration of a formalin solution of 0.005%, or 0.01%, or 0.015%, or 0.02%, or 0.025%, or 0.03%, or 0.035%. An immunogenic composition may have, according to some embodiments, a concentration of a formalin solution of about 0.005%, or about 0.01%, or about 0.015%, or about 0.02%, or about 0.025%, or about 0.03%, or about 0.035%. In some embodiments, an immunogenic composition may have a concentration of a formalin solution of about 0.005% to about 0.035%, or about 0.01% to about 0.03%, or about 0.015% to about 0.025%, or about 0.015% to about 0.02%, or about 0.01% to about 0.02%.

According to some embodiments, an immunogenic composition (e.g., an immunogenic composition for use in breast cancer treatment) may comprise an immunoactive material (e.g., an antigen), an immune response activator (e.g., a BCG vaccine), and an immune response mitigator (e.g., formalin). An immunogenic composition may comprise any desirable components to preserve, stabilize, sterilize, or sterilize such compositions. Additional components may comprise antibiotics, antifungal agents, gelatin, monosodium glutamate, thimerosal, or any combination thereof.

An immunogenic composition may be a solution suitable for injection in a patient (e.g., a human subject, a mouse subject).

Methods of Preparing an Immunogenic Composition

According to some embodiments, the present disclosure relates to a method of producing an immunogenic composition that may be used as an immunotherapy for the treatment of cancer (e.g., breast cancer in a human subject).

FIG. 1 shows a flow diagram illustrating a method of preparing an immunogenic composition, according to a specific embodiment of the disclosure.

As shown in FIG. 1, in some embodiments, a method of producing an immunogenic composition 100 may include harvesting 105 a tumor tissue (e.g., a mass of neoplastic breast tissue) from a subject to generate a harvested tissue. A tumor tissue may be harvested at any stage of tumor development. In some embodiments, a stage of tumor development at which tumor tissue is harvested may be selected based on a quantity of different antigens present in the tumor tissue during the stage of development, an abundance of a selected antigen in the tumor tissue during the stage of development, or both.

In some embodiments, harvesting 105 may include harvesting a tumor tissue from a tissue culture, for example a tissue culture derived from a subject's neoplastic breast tissue to generate a harvested tissue. A tumor tissue may be harvested from any form of tissue culture, including but not limited to a primary culture, a two-dimensional monolayer culture, an explant-cell culture, a precision-cut slice culture, a three-dimensional cell culture, a culture derived from partial enzymatic degradation of stromal cells, a sandwich culture, or any other appropriate culturing method. In some embodiments, a tumor tissue may be harvested directly without intervening tissue culture (e.g., in human patients).

A method of producing an immunogenic composition 100 may include fragmenting 110 a harvested tissue, according to some embodiments, to form a tissue fragment. Fragmenting 110 a harvested tumor tissue may include cutting a harvested tissue into one or more tissue fragments of an appropriate size and mass. Fragmenting 110 a harvested tissue may include any method of dividing a the harvested tissue into smaller sections, including cutting, mincing, dicing, chopping, cleaving, clipping, severing, slashing, shearing, hewing, chipping, ripping, tearing, dividing, cropping, hacking, slicing, grinding, or any similar action. Various tools may be used in fragmenting a harvested tissue including, but not limited to a scalpel, a knife, a scissor, a saw, a laser, a water jet cutter, a wire, a chipper, a razor, a grinders, a blender, a shear, a pincers, a blades, or any combination thereof.

A method of producing an immunogenic composition 100 may include storing 115 a tissue fragment, according to some embodiments. A tissue fragment, in some embodiments, may be combined with a storage solution prior to storing 115. A storage solution may include dimethyl sulfoxide (DMSO), Bovine Calf Serum (BCS), Fetal Bovine Serum (FBS), Dulbecco's Modified Eagle Medium (DMEM), Eagle's minimal essential medium, glycerol, Human Serum Albumin, Roswell Park Memorial Institute medium (RPMI-1640), Ham's F-10 nutrient mix (Ham F10), phosphate buffered saline (PBS), combinations thereof, or any other storage solution suitable for preservation. In some embodiments, a storage solution may include one or more cryoprotectants. A cryoprotectant, in some embodiments, may include ethylene glycol, propylene glycol, glycerol, glucose, DMSO, polyvinyl-pyrrolidone, methanol, methyl acetamide, a polyol, or any combination thereof. According to some embodiments, a storage solution may include one or more antibiotic or antifungal agents including for example penicillin, gentamicin, ciprofloxacin, enrofloxacin, tiamulin, minocycline, quinolone derivatives, streptomycin, kanamycin, nystatin, amphotericin, or any combination thereof. Specific concentrations of cryprotectants and antibiotics/antifungals may vary depending on specific storage considerations (e.g., storage temperature, length of storage time). According to some embodiments, a storage solution may be selected based on specific characteristics of a subject (e.g., subject allergy to a specific antibiotic). According to some embodiments, a storage solution may include PBS, penicillin (e.g., 2000 IU/mL), and gentamicin (e.g., 250 µg/mL).

According to some embodiments, storing 115 a tissue fragment may include storage at temperatures below room temperature (e.g., cryogenic temperatures). Storage of a tissue fragment may occur at temperatures of $\leq -196°$ C., or $\leq -180°$ C., or $\leq -160°$ C., or $\leq -140°$ C., or $\leq -100°$ C., or $\leq -80°$ C. In some embodiments, storing 105 a tissue fragment may include storing a tissue fragment at about minus 80° C.

As shown in FIG. 1, a method of producing an immunogenic composition 100 may include washing 120 a tissue fragment. Washing 120 may be performed prior to storing 115 a tissue fragment, in lieu of storing 115 a tissue fragment, or after storing 115 a tissue fragment. Washing 120 a tissue fragment may be performed using a wash solution. In some embodiments, a wash solution may include dimethyl sulfoxide (DMSO), Bovine Calf Serum (BCS), Fetal Bovine Serum (FBS), Dulbecco's Modified Eagle Medium (DMEM), Eagle's minimal essential medium, glycerol, Human Serum Albumin, Roswell Park Memorial Institute medium (RPMI-1640), Ham's F-10 nutrient mix (Ham F10), phosphate buffered saline (PBS), or any combination thereof. According to some embodiments, a wash solution and a storage solution may have the same composition. In some embodiments, a washing solution may include one or more antibiotic or antifungal agents including for example penicillin, gentamicin, ciprofloxacin, enrofloxacin, tiamulin, minocycline, quinolone derivatives, streptomycin, kanamycin, nystatin, amphotericin, or any combination thereof.

Washing 120 a tissue fragment may include exposing at least one surface of the tissue fragment to a wash solution, according to some embodiments. In some embodiments, washing 120 a tissue fragment may include cascading, showering, spraying, misting, fogging, pouring, dripping, or any combination thereof a wash solution onto at least one surface of a tissue fragment. According to some embodiments, washing 120 a tissue fragment may include soaking the tissue fragment in a volume of a wash solution such that at least one surface of the tissue fragment contacts the wash solution.

According to some embodiments, washing 120 a tissue fragment may include removing a washing solution from the tissue fragment. Removing a washing solution from a tissue fragment may include blotting the tissue fragment with an absorbent material (e.g., sterile gauze) or exposure of the tissue fragment to a mechanism of forced-air drying and/or open air drying.

In some embodiments, washing 120 a tissue fragment may include: (a) submerging the tissue fragment in a wash solution of PBS plus penicillin (e.g., 2000 IU/mL), and gentamicin (e.g., 250 µg/mL), (b) removal of the tissue fragment from the wash solution, and (c) blotting the tissue fragment with a dry, sterile gauze.

As shown in FIG. 1, a method of producing an immunogenic composition 100 may include homogenizing 125 a tissue fragment to form a cell homogenate. According to some embodiments, homogenizing 125 a tissue sample may include adding a suspension solution to a tissue sample. A suspension solution may include dimethyl sulfoxide (DMSO), Bovine Calf Serum (BCS), Fetal Bovine Serum (FBS), Dulbecco's Modified Eagle Medium (DMEM), Eagle's minimal essential medium, glycerol, Human Serum Albumin, Roswell Park Memorial Institute medium (RPMI-1640), Ham's F-10 nutrient mix (Ham F10), phosphate buffered saline (PBS), or any combination thereof. According to some embodiments, a suspension solution may have the same composition as a wash solution, a storage solution, or both. In some embodiments, a suspension solution may include one or more antibiotic or antifungal agents including for example penicillin, gentamicin, ciprofloxacin, enrofloxacin, tiamulin, minocycline, quinolone derivatives, streptomycin, kanamycin, nystatin, amphotericin, or any combination thereof.

According to some embodiments, homogenizing 125 a tissue fragment may include cutting, slicing, fragmenting, mincing, pulverizing, blending, grinding, macerating, or any combination thereof. Homogenizing 125 a tissue sample may include using a glass homogenizer, in some embodiments. In some embodiments, homogenizing 125 a tissue sample may include pulverizing the tissue sample using at least 8 strokes, or at least 10 strokes, or at least 12 strokes, or at least 14 strokes, or at least 16 strokes, or at least 18 strokes, or at least 20 strokes of a glass homogenizer to form a cell homogenate.

According to some embodiments, homogenizing 125 a tissue sample may include adding a suspension solution to a tissue sample. A suspension solution may include dimethyl sulfoxide (DMSO), Bovine Calf Serum (BCS), Fetal Bovine Serum (FBS), Dulbecco's Modified Eagle Medium (DMEM), Eagle's minimal essential medium, glycerol, Human Serum Albumin, Roswell Park Memorial Institute medium (RPMI-1640), Ham's F-10 nutrient mix (Ham F10), phosphate buffered saline (PBS), or any combination thereof. According to some embodiments, a suspension solution may have the same composition as a wash solution, a storage solution, or both. In some embodiments, a suspension solution may include one or more antibiotic or antifungal agents including for example penicillin, gentamicin, ciprofloxacin, enrofloxacin, tiamulin, minocycline, quinolone derivatives, streptomycin, kanamycin, nystatin, amphotericin, or any combination thereof.

In some embodiments, homogenizing 125 a tissue sample may include combining one or more tissue samples in a volume of a suspension solution based on a desired ratio of tissue sample mass per milliliter of suspension solution (gram of tissue sample per mL of suspension solution). In some embodiments, a desired ratio of tissue sample mass per milliliter of suspension solution may be about 0.3 g/mL, or about 0.4 g/mL, or about 0.5 g/mL, or about 0.6 g/mL, or about 0.7 g/mL, according to some embodiments. In some embodiments, homogenizing a tissue sample may include combining one or more tissue fragments having a combined mass of about 0.5 g with 1 mL of a suspension solution of PBS and pulverizing with a glass homogenizer.

As shown in FIG. 1, a method of producing an immunogenic composition 100 may include separating 130 an immunoactive material (e.g., a tumor antigen) from a cell homogenate. In some embodiments separating 130 an immunoactive material (e.g., a tumor antigen) from a cell homogenate may include separation of the cell homogenate to form a supernatant and a precipitate, where the supernatant includes a protein composition including an immunoactive material (e.g., a tumor antigen). Any number of techniques may be used in separating 130 an immunoactive material from a cell homogenate. According to some embodiments, separating 130 an immunoactive material (e.g., a tumor antigen) from a cell homogenate may include centrifugation, ultracentrifugation, filtration, microfiltration, sedimentation, isolation, purification, or any combination thereof.

According to some embodiments, separating an immunoactive material (e.g., a tumor antigen) from a cell homogenate may include centrifugation of the cell homogenate to for a supernatant and a precipitate, where the supernatant includes a protein composition including an immunoactive material (e.g., a tumor antigen). In some embodiments, centrifugation may be performed at a centrifugal force of about 250 g for a length of about 10 minutes. Variations in the speed and length of centrifugation may be applied as appropriate to separate an immunoactive material (i.e., present in a supernatant) from cellular debris (i.e., a precipitate).

As shown in FIG. 1, a method of producing an immunogenic composition 100 may include quantifying 135 a protein concentration of a supernatant (e.g., retaining an immunoactive material). Any suitable technique may be used to quantify a protein concentration of a supernatant. A supernatant protein concentration may be quantified, for example using a Bradford Assay, a Folin-Lowry assay, a bis-cinchoninic acid assay, a Kjeldahl assay, a Biuret method, ultraviolet absorption quantification, fluorescence emission quantification, amino acid analysis via RP-HPLC, radiolabelling, Edman degradation, RP-chromatography, or any combination thereof.

As shown in FIG. 1, a method of producing an immunogenic composition 100 may include mixing 140 a volume of supernatant containing a desired quantity of protein (e.g., an immunoactive material), a volume of an immune response activator (e.g., a BCG vaccine), and a volume of an immune response mitigator (e.g., formalin) to form the immunogenic composition.

According to some embodiments, mixing 140 may include selecting a volume of supernatant such that an immunogenic composition has a final concentration of about 6 mg of a supernatant protein per kg of a subject's weight (mg/kg), or about 6.5 mg/kg, or about 7 mg/kg, or about 7.5 mg/kg, or about 8 mg/kg, or about 8.5 mg/kg, or about 9 mg/kg, or about 9.5 mg/kg, or about 10 mg/kg, where about represents 10%. In some embodiments, mixing 140 may include selecting a volume of supernatant such that an immunogenic composition has a final concentration of about 6 mg of a supernatant protein per kg of a subject's weight (mg/kg) to about 10 mg/kg, or about 6.5 mg/kg to about 9.5 mg/kg, or about 7 mg/kg to about 9 mg/kg, or about 7.5 mg/kg to about 8.5 mg/kg, or about 8 mg/kg to about 10 mg/kg.

In some embodiments, mixing 140 may include selecting a volume of an immune response activator (e.g., a BCG vaccine) such that an immunogenic composition has a final concentration of about of 0.525 mg of the immune response activator per mL of immunogenic composition (mg/mL), or 0.50 mg/mL, or 0.575 mg/mL, or 0.60 mg/mL, 0.625 mg/mL, or 0.650 mg/mL, or 0.675 mg/mL, or 0.70 mg/mL, or 0.725 mg/mL, according to some embodiments. According to some embodiments, mixing 140 may include selecting a volume of an immune response activator (e.g., a BCG vaccine) such that an immunogenic composition has a final concentration of about 0.525 mg of BCG per mL of immunogenic composition (mg/mL) to about 0.725 mg/mL, or about 0.550 mg/mL to about 0.725 mg/mL, or about 0.575 mg/mL to about 0.70 mg/mL, or about 0.60 mg/mL to about 0.675 mg/mL, or about 0.625 mg/mL to about 0.675 mg/mL, or about 0.60 mg/mL to about 0.65 mg/mL where about represents plus or minus 10%.

Mixing 140, in some embodiments, may include selecting a volume of an immune response mitigator (e.g., formalin) such that an immunogenic composition has a final concentration of a formalin solution of 0.005%, or 0.01%, or 0.015%, or 0.02%, or 0.025%, or 0.03%, or 0.035%. In some embodiments, mixing 140, in some embodiments, may include selecting a volume of an immune response mitigator (e.g., formalin) such that an immunogenic composition has a final concentration of a formalin solution of about 0.005% to about 0.035%, or about 0.01% to about 0.03%, or about 0.015% to about 0.025%, or about 0.015% to about 0.02%, or about 0.01% to about 0.02%.

Methods of Treating a Cancer Subject with an Immunogenic Composition

It may be desirable, in some embodiments, to administer to a subject an immunogenic composition comprising one or more allogenic antigens to the subject (e.g., antigens harvested from the intended subject, copies of the antigens in a tissue of the subject) for the treatment of cancer (e.g., breast cancer).

According to some embodiments, a method of treating a cancer subject (e.g., a breast cancer subject) may include: (a) preparing an immunogenic composition by mixing a volume of a supernatant containing a desired quantity of protein (e.g., an immunoactive material), a volume of an immune response activator (e.g., a BCG vaccine), and a volume of an immune response mitigator (e.g., formalin) to form an immunogenic composition and (b) applying the immunogenic composition in a muscular region adjacent to a cancerous tissue (e.g., a deltoid region of a breast cancer subject).

Embodiments of an immunogenic composition and methods of preparing an immunogenic composition are disclosed in other portions of this specification. According to some embodiments, a method of treating a cancer subject (e.g., a breast cancer subject) with an immunogenic composition includes preparing the immunogenic composition immediately prior to patient treatment. In some embodiments, an immunogenic composition may be prepared ≥one hour before subject treatment, or ≥30 minutes of subject treatment, or ≥20 minutes of subject treatment, or ≥15 minutes of treatment, or ≥10 minutes of treatment, or ≥5 minutes of subject treatment, or ≥3 minutes of subject treatment.

A method of treating a cancer subject, in some embodiments, may include injecting an immunogenic composition intradermally into a region adjacent to a tumor tissue. A method of treating a breast cancer subject, according to some embodiments, may include injecting an immunogenic composition intradermally into a deltoid region of the breast cancer subject. According to some embodiments, a cancer subject may be injected with an immunogenic composition intradermally into a region adjacent to a tumor tissue in one or more doses over any desired fixed or variable interval (e.g., every six weeks for at least 18 weeks.) According to some embodiments, a cancer subject may be injected with one dose, or two doses, or three doses or four doses, or five does, or six doses, or seven doses, or eight doses, or nine doses, or ten doses of an immunogenic composition. A cancer subject may be injected with a dose of an immunogenic composition every two-weeks, or every three weeks, or every four weeks, or every five weeks, or every six weeks, or every seven weeks, or every eight weeks, or every nine weeks, or every ten weeks, according to some embodiments. In some embodiments, a breast cancer subject may be injected with an immunogenic composition intradermally into a deltoid region every six weeks for at least 18 weeks. An immunogenic composition, in some embodiments, may be prepared immediately prior (e.g., ≥one hour) to treatment of a cancer subject. Treatment of a cancer subject (e.g., a breast cancer subject) with an immunogenic composition may be performed in addition to or in lieu of other medical procedures for the treatment of cancer, including but not limited to surgery, other immunotherapies, chemotherapy, and/or radiation.

As will be understood by those skilled in the art who have the benefit of the instant disclosure, other equivalent or alternative compositions of an immunogenic composition, methods of preparing an immunogenic composition, and/or methods of treating a cancer subject (e.g., a breast cancer subject) with an immunogenic composition can be envisioned without departing from the description contained herein. Accordingly, the manner of carrying out the disclosure as shown and described is to be construed as illustrative only.

Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Where open terms such as "having" or "comprising" are used, one of ordinary skill in the art having the benefit of the instant disclosure will appreciate that the disclosed features or steps optionally may be combined with additional features or steps. Such option may not be exercised and, indeed, in some embodiments, disclosed compositions and/or methods may exclude any other features or steps beyond those disclosed herein. Elements, compositions, devices, systems, methods, and method steps not recited may be included or excluded as desired or required. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/− about 10%, depicted value +/−about 50%, depicted value +/−about 100%) and/or a range endpoint. With respect to the former, a value of 50 depicted in an example, table, and/or drawing may form the basis of a range of, for example, about 45 to about 55, about 25 to about 100, and/or about 0 to about 100. Disclosed percentages are weight percentages except where indicated otherwise.

Equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

EXAMPLES

Some specific example embodiments of the disclosure may be illustrated by one or more of the examples provided herein.

Example 1: Preparing an Immunogenic Composition for Mouse Subjects

A group of mice were induced to produce tumors by injecting $8 \times 10^5$ 4T1 cells per mouse into their mammary glands. After tumor formation, the mice were euthanized and tumor tissue was harvested. The harvested tissue divided into samples of approximately 1 g each and then cut into pieces approximately 300 to 400 mg in mass, and each sample was placed in a storage solution of PBS (4.45 mM $Na_2HPO_4$, 1.55 mM $NaH_2PO_4$, 137 mM NaCl, pH 7.2) with 2000 IU/ml Penicillin and 25 g/ml Gentamicin. The tissue samples were stored at −80° C. until the time of preparation of the immunogenic composition.

Just prior to treatment, a tissue sample was placed in a petri dish and submerged in a cold wash solution of in a storage solution of PBS (4.45 mM $Na_2HPO_4$, 1.55 mM $NaH_2PO_4$, 137 mM NaCl, pH 7.2) with 2000 IU/ml Penicillin and 25 g/ml Gentamicin. Each tissue sample was blotted with sterile gauze to remove excess wash solution. Each tissue sample was fragmented into pieces approximately 2 to 3 mm in size. A suspension solution of PBS was added to the tissue sample at a ratio of 1 mL of PBS per 0.5 g of tissue. The tissue samples were then independently homogenized using 10 strokes of a glass homogenizer to form cell homogenates. Each cell homogenate was centrifuged at 250 g for 10 minutes to generate a supernatant and a precipitate. A Bradford Assay was used to quantify the protein concentration of each supernatant.

An immunogenic composition was prepared for each mouse subject using the supernatant prepared from the tissue sample by mixing the following: (a) a volume of supernatant such that the immunogenic composition contained 220 mg of supernatant protein per mouse subject (each mouse subject having a mass of approximately 20 to 25 g), (b) 0.6 mL of a 15% BCG (Danish live attenuated strain) solution a volume of BCG (Danish live attenuated strain), and (c) a formaldehyde solution such that the immunogenic composition had a concentration of 0.02% by volume.

Example 2: Treatment of Mouse Breast Cancer Subjects

Fifteen six-week old BALB/c mice were divided into groups. Group one contained five mice who were tumor-free (safety control). Group 2 included five mice who were induced to develop mammary tumors and would not receive any treatment (control). Group 3 included five mice who were induced to develop mammary tumors and received immunotherapy treatment (treatment group).

Each of the mice in Group 3 received intradermal injections in the dorsal region of the neck with a 0.1 mL dose of the immunogenic composition beginning 15 days after tumor induction (tumors were palpable). Subsequent doses were given at one-week intervals with the immunogenic composition being prepared immediately prior to each treatment. The Group 3 mouse patients received four total doses over a four-week period (one dose per week).

All five of the Group 1 mice (tumor-free) were alive 3 months after the initiation of the study (the first day on which the Group 2 and Group 3 mice were induced for tumor production and 15 days prior to the first dose of immunogenic composition). All five of the mice in Group 2 (untreated tumor-induced) perished within 45 days of the initiation of the study. All the mice in Group 3 (treated tumor-induced) were alive 3 months after the initiation of the study with tumors that were significantly diminished or intangible.

Example 3: Preparing an Immunogenic Composition for Human Subjects

Neoplastic breast tissue (i.e., tumor tissue) was harvested from a group of twenty subjects each with advanced stage breast cancer. Six of the subjects elected to receive only immunotherapy (Group I). Fourteen of the subjects were designated to receive a combination of chemotherapy/radiotherapy and immunotherapy (Group II).

The harvested tissue divided into samples of approximately 300 to 400 mg in mass, and each sample was placed in a storage solution of PBS (4.45 mM $Na_2HPO_4$, 1.55 mM $NaH_2PO_4$, 137 mM NaCl, pH 7.2) with 2000 IU/ml Penicillin and 25 g/ml Gentamicin. The tissue samples were stored at −80° C. until the time of preparation of the immunogenic composition.

Just prior to treatment, a tissue sample from each subject was placed in a petri dish and submerged in a cold wash solution of in a storage solution of PBS (4.45 mM $Na_2HPO_4$, 1.55 mM $NaH_2PO_4$, 137 mM NaCl, pH 7.2) with 2000 IU/ml Penicillin and 25 g/ml Gentamicin. Each tissue sample was blotted with sterile gauze to remove excess wash solution. Each tissue sample was fragmented into pieces approximately 2 to 3 mm in size. A suspension solution of PBS was added to the tissue sample at a ratio of 1 mL of PBS per 0.5 g of tissue. The tissue samples were then independently homogenized using 10 strokes of a glass homogenizer to form cell homogenate. Each cell homogenate was centrifuged at 250 g for 10 minutes to generate a supernatant and a precipitate.

An immunogenic composition was prepared for each subject by mixing the supernatant prepared from their respective tissue samples with 0.06 mL of a 15% BCG (Danish live attenuated strain) solution and a formaldehyde solution such that the immunogenic composition had a concentration of 0.02% by volume.

Example 4: Treatment of Human Breast Cancer Subjects

Each of the subjects in Group I (six subjects electing to receive only immunotherapy) and Group 2 (fourteen subjects designated to receive a combination of chemotherapy/radiotherapy and immunotherapy) were intradermally injected in their deltoid region with a 0.5 mL dose of an immunogenic composition prepared using their neoplastic breast tissue sample. Subsequent doses were given at six-week intervals with the immunogenic composition being prepared immediately prior to each treatment. All patients received three total doses over an 18 week period (one dose every six weeks).

Group 1 (immunotherapy only) had an estimated survival rate of 83.3%. This high rate was likely skewed due to the small number of subjects. Group 2 (chemotherapy/radiation/other immunotherapies and immunotherapy combination) had an survival rate of 50%. All human subjects who received treatment with an immunogenic composition prepared using their neoplastic breast tissue sample displayed an increase in immune response as evaluated using an intradermal tuberculin test. Treated patients reported fewer side effects than statistically reported by patients receiving only chemotherapy/radiation treatment.

Example 5: Preparing an Immunogenic Composition for Mouse Subjects

Six- to eight-week-old female BALB/c mice were provided by José Maria Vargas Medical School (Universidad Central de Venezuela) and maintained in their animal facility. This study was approved by the Bioethics Committee of José Maria Vargas Medical School. 4T1 murine mammary cell line was purchased from the American Type Culture Collection and maintained in the recommended medium.

Ten female BALB/c mice were inoculated with 4T1 cells to obtain tumor tissue to prepare autologous tumor homogenate. The 4T1 cells were harvested using 0.25% trypsin (Sigma-Aldrich) in 0.05% EDTA (EMD Millipore Corporation), washed with RPMI-1640 (MP Biomedicals LLC) and resuspended in 1× phosphate buffer saline (PBS). Viability of cells was determined by 0.25% trypan blue dye exclusion. 4T1 cells (1×106) were injected subcutaneously (s.c) into the mammary fat pad of female Balb/c mice. When tumors reached a volume of 1,5-2,5 cm3, mice were anesthetized with xylazine/ketamine until unresponsive to toe tap and/or agonal breathing and sacrificed. Primary tumors were extracted in sterile conditions and stored at −80° C. in PBS plus penicillin-streptomycin 1× (Sigma-Aldrich). Tumors (0.5 gr) were washed in PBS plus penicillin-streptomycin 1× and then mechanically macerated in a homogenizer with sterile PBS (1 mL). The cell homogenate was centrifuged for 10 minutes at 250 g. The supernatant fraction was taken and proteins were quantified by Bradford's method. One vial of BCG (live attenuated Danish strain 1331; Staten Serum Institute, Copenhagen) was dissolved in 200 µL of Sauton diluent. Sixty microliters of this solution was added to 300 µL of cell homogenate plus 0.02% formaldehyde (Fisher Scientific), constituting the BCG/formalin/autologous tumor homogenate vaccine.

BCG (live attenuated Danish strain 1331; Staten Serum Institute, Copenhagen) was prepared by dissolving one vial of BCG in 200 µL of Sauton diluent.

The Group 1 treatment (G1) was prepared as PBS only. The Group 2 treatment (G2) was prepared as a BCG/formalin composition comprising a final concentration of 0.0625 mg BCG and 0.02% formaldehyde per mouse. The Group 3 treatment (G3) was prepared as a BCG/cell homogenate composition comprising a final concentration of 0.0625 mg BCG and 200 µg of cell homogenate per mouse. The Group 4 treatment (G4) was prepared as a BCG/formalin/autologous tumor homogenate vaccine comprising a final concentration of 0.0625 mg BCG, 200 µg of cell homogenate, and 0.02% formaldehyde per mouse.

Example 6: Treatment of Mouse Breast Cancer Subjects

Treatment mice were prepared by subcutaneously (s.c.) injecting 4T1 cells ($1\times10^6$) into female BALB/c mice. The 4T1 cells were harvested using 0.25% trypsin (Sigma-Aldrich) in 0.05% EDTA (EMD Millipore Corporation), washed with RPMI-1640 (MP Biomedicals LLC) and resuspended in 1× phosphate buffer saline (PBS). Viability of cells was determined by 0.25% trypan blue dye exclusion. 4T1 cells ($1\times10^6$) were injected subcutaneously (s.c) into the mammary fat pad of female BALB/c mice.

Mouse treatments were initiated five days after the injection of the 4T1 tumor cells. The BALB/c mice (n=20) were randomly assigned into four groups of five animals each: group 1 (G1) tumor mice were given PBS (negative control); group 2 (G2) tumor mice were given a BCG/formalin composition (0.0625 mg/mouse, formaldehyde: 0.02%/mouse); group 3 (G3) tumor mice were given a BCG/cell homogenate composition (0.0625 mg BCG/mouse) plus 200 µg cell homogenate/mouse); and group 4 (G4) tumor mice were given a BCG/formalin/autologous tumor homogenate vaccine (BCG: 0.0625 mg/mouse, Cell homogenate protein: 200 µg/mouse, formaldehyde: 0.02%). One hundred microliters of each treatment were injected s.c on the base of the neck of each mouse. The treatment schedule consisted of one weekly-injected dose for four weeks. The tumor volume was measured every 4 days up to 28 days post tumor cell injection in $mm^3$ using the method described in Feldman et al., A mathematical model for tumour volume evaluation using two-dimensions, J. Quant Appl Method 2009, 4(4): 455-462 and expressed in $mm^3$. Tumor growth rate was calculated as a percentage of volume increase with respect to the initial volume.

Example 7: Treatment of Tissue Harvested from Mouse Breast Cancer Subjects

Five weeks after tumor cell inoculation of the BALB/c mice, the mice from Groups 1-4 were euthanized and their respective tumors were subjected to pathologic examination. Tissues were fixed in 4% w/v formaldehyde, paraffin-embedded, and sections were cut at 5 µm intervals and stained with Hematoxylin, eosine, and Gomori's trichome. Immunohistochemistry was carried out according to Mihara H, Boudaka A, et al, Transient receptor potential vanilloid 4 (TRPV4)-dependent calcium influx and ATP release in mouse oesophageal keratinocytes, J Physiol 2011, 589(Pt 14):3471-82. Primary antibodies against CD209b, CD49b, CD68, CD4, CD19, Gr-1, IFN-γ, CD8-α, TGF-β, CD11b were used. The nuclei were stained with DAPI and the slides were mounted with a DABCO containing medium. Observation was carried out using a fluorescent microscope Eclipse E600light, equipped with epifluorescence illumination. Slides were digitally photographed with a SPOT Flex FX1520 camera and ImageJ software (version 1.46r) was used for image analysis. The measurements of the amount of fluorescence for TGF-β were carried out by integrated optical density (IOD), as reported by Ahn AH and Basbaum AI, Tissue injury regulates serotonin 1D receptor expression: implications for the control of migraine and inflammatory pain, J Neurosci 2006, 26(32):8332-8.

The cellularity was determined as described in Tzekov R, Quezada A, et al., Repetitive mild traumatic brain injury causes optic nerve and retinal damage in a mouse model, J Neuropathol Exp Neurol 2014, 73(4):345-61, and results were expressed as number of cells/1000 $\mu m^2$. Neutrophil infiltration and mitotic indexes were completed in accordance with the diclosures of Ysebaert D K, De Greef K E, et al., Identification and kinetics of leukocytes after severe ischaemia/reperfusion renal injury, Nephrol Dial Transplant 2000, 15(10):1562-74 and Pirog E C and Czerwinski W., Diagnostic and prognostic significance of the mitotic index in endometrial adenocarcinoma, Gynecol Oncol 1992, 46(3):337-40, respectively. Collagen was localized and quantified using the procedure disclosed in Kim S M, Park K C, et al., Effect of selective cyclooxygenase-2 inhibitor meloxicam on liver fibrosis in rats with ligated common bile ducts, Hepatol Res 2008, 38(8):800-9. Necrotic areas in tumor sections were determined using the methods disclosed in Moffitt P., A methyl green-pyronin technique for demonstrating cell death in the murine tumour S180, Cell Biol Int 1994, 18(6):677-9. BCG staining was performed based on the methods disclosed by Mote R F, Muhm R L, and Gigstad D C, A staining method using acridine orange and auramine O for fungi and mycobacteria in bovine tissue, Stain Technol 1975, 50(1):5-9.

Kruskal-Wallis non-parametric test was performed followed by Tukey's post hoc. Pearson's correlation test were used for association analyses. The PAST statistical program was used and statistical significance was met for a levels of 0.05, two-tailed.

Example 8: Results of Treatment of Mouse Breast Cancer Subjects-Tissue Imaging Imaging of the harvested tumors from the G1, G2, G3, and G4 treatment groups showed that the 4T1 tumors are enveloped by sheets of dense connective tissue, presenting an infiltration of mononuclear and polymorphonuclear cells. FIG. 2A illustrates microscopic imaging of a tumor proliferative zone (Z1) harvested from a representative G1 treatment mouse and stained with Hematoxylin and eosine (H&E staining) as described in EXAMPLE 7. The bar represents 20 m. A Z1 proliferative zone is characterized by cells in constant mitosis (arrows) with large nuclei and scarce cytoplasm.

Figure 2A:
FIG. 2A illustrates microscopic imaging of a tumor proliferative zone (Z1) harvested from a G1 treatment mouse, according to a specific example embodiment of the disclosure.

FIG. 2B illustrates microscopic imaging of zone 2 (Z2) harvested from a representative G1 treatment mouse and exposed to H&E staining. The bar represents 20 m. Arrows indicate neutrophils. A Z2 proliferative zone is characterized by the presence of large lymphatic vessels, blood vessels, and tumor cells where, as a consequence of cell unions degradation, mediated by neutrophil metalloproteases, tumor cells migrate via lymphatic and blood vessels, and induce metastasis.

Figure 2D:
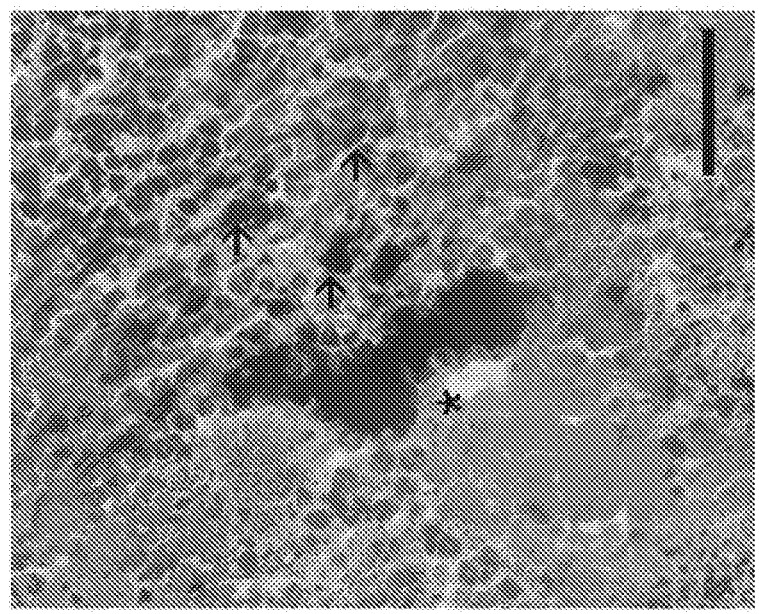
FIG. 2D illustrates microscopic imaging of a tumor necrosis zone from a G4 treatment group tissue, according to a specific example embodiment of the disclosure.
Figure 2C:
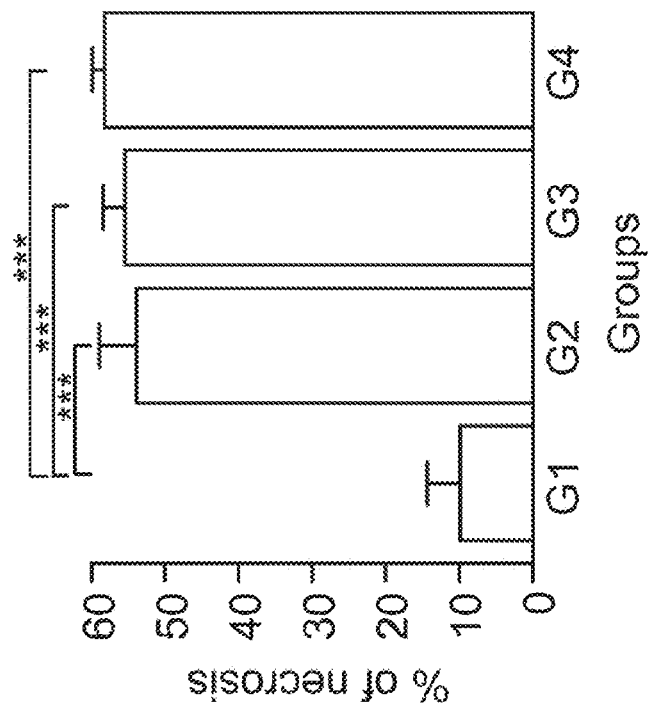
FIG. 2C is a bar graph illustrating the percent of necrosis present in the tissue harvested from treatment groups G1, G2, G3, and G4, according to a specific example embodiment of the disclosure.

Microscopic imaging with H&E staining showed that 4T1 tumors had a necrotic core caused by hypoxic conditions due to accelerated tumor growth. Necrosis was quantified using the methods described in EXAMPLE 7. The G2, G3, and G4 treatment groups had significantly higher levels of necrosis compared to the G1 (control group), as shown in FIG. 2C. The data is shown as the mean SEM of five mice per group (***, p≤0.001).

Evaluation shows that necrosis is a long-term process, beginning in the tumor core and extending to the outer side and thereby generating necrotic zones surrounded by infiltrating leukocytes with lipofucsin bodies. FIG. 2D illustrates a microscopic image of a tumor necrosis zone from a G4 treatment group tissue stained with H&E and showing necrotic zones surrounded by infiltrating leukocytes (indicated by asterisks) with lipofuscin bodies (indicated by arrows). The bar represents 30 μm.

Figure 2F:
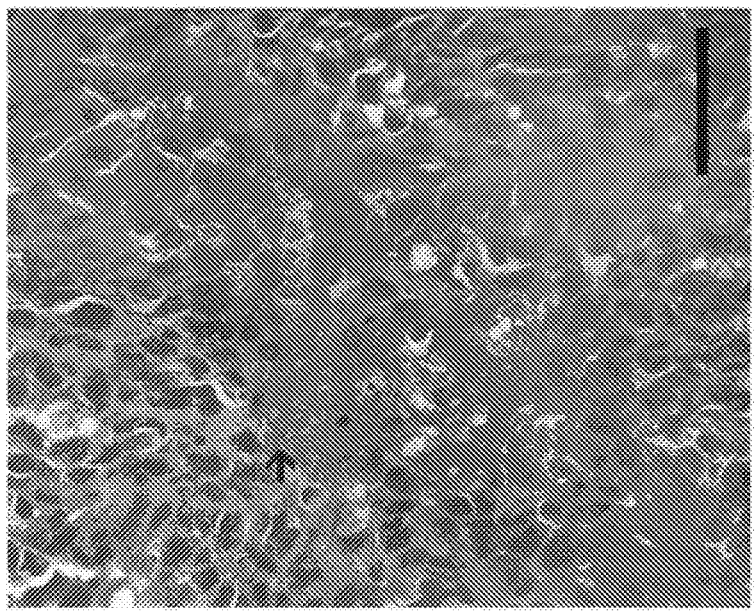
FIG. 2F illustrates microscopic imaging of necrotic foci with leukocytes infiltration from a G3 treatment group tissue, according to a specific example embodiment of the disclosure.
Figure 2E:
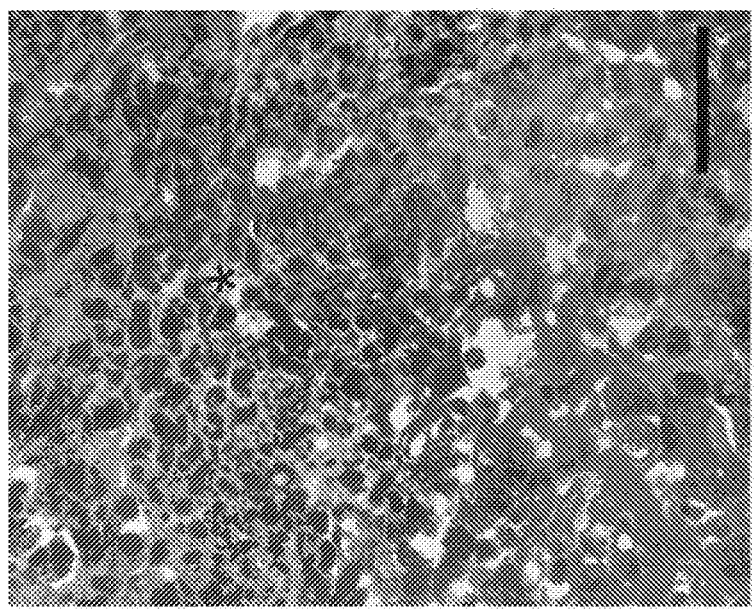
FIG. 2E illustrates microscopic imaging of necrotic foci with leukocytes infiltration from a G2 treatment group tissue, according to a specific example embodiment of the disclosure.
Figure 2G:
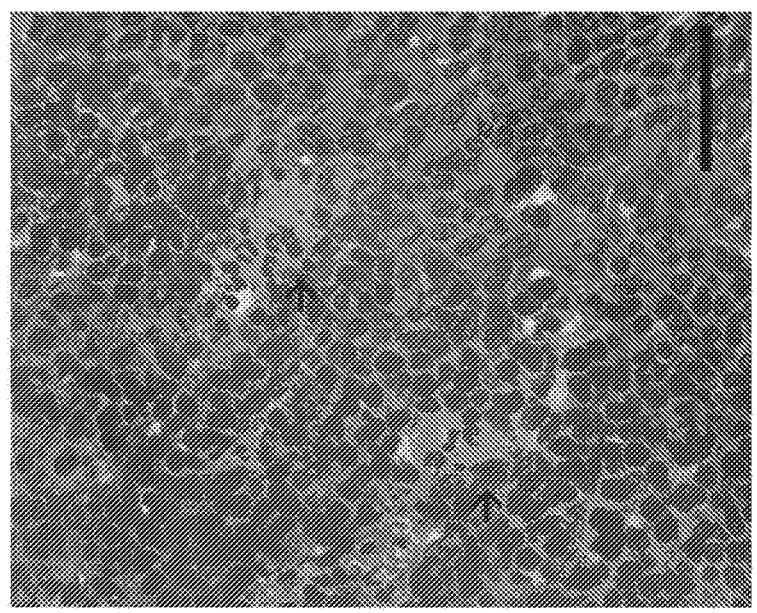
FIG. 2G illustrates microscopic imaging of necrotic foci with leukocytes infiltration from a G4 treatment group tissue, according to a specific example embodiment of the disclosure.

Particular patterns of necrosis were found in each treatment group. G1 showed a coagulative necrosis located in the core area that was poorly infiltrated. As illustrated in FIG. 2E (G2 treatment), FIG. 2F (G3 treatment), and FIG. 2G (G4 treatment), microscopic imaging with H&E staining showed that tissue harvested from the G2, G3, and G4 treatment groups presented necrotic foci with eosinophilic material, neutrophilic infiltration, and cellular debris. Particularly in treatment group G3 (FIG. 2F) and treatment group G4 (FIG. 2G), imaging showed lytic necrosis (indicated by an arrow in FIG. 2F) with eosinophilic material, lysed cells, and minimal mononuclear cell infiltration (indicated by an arrow in FIG. 2G). The bars illustrated in FIGS. 2E, 2F, AND 2G represent 20 m.

Tumor slides were processed for immunohistochemistry, as described in EXAMPLE 7, and stained with H&E and Gomori's trichome, to determine TGF-β positive cells, collagen fibers distribution and collagen concentration, respectively. FIGS. 3B and 3D illustrate tissues stained with H&E. FIGS. 3C and 3E illustrate tissues stained with Gomori's trichome.

Figure 3A:
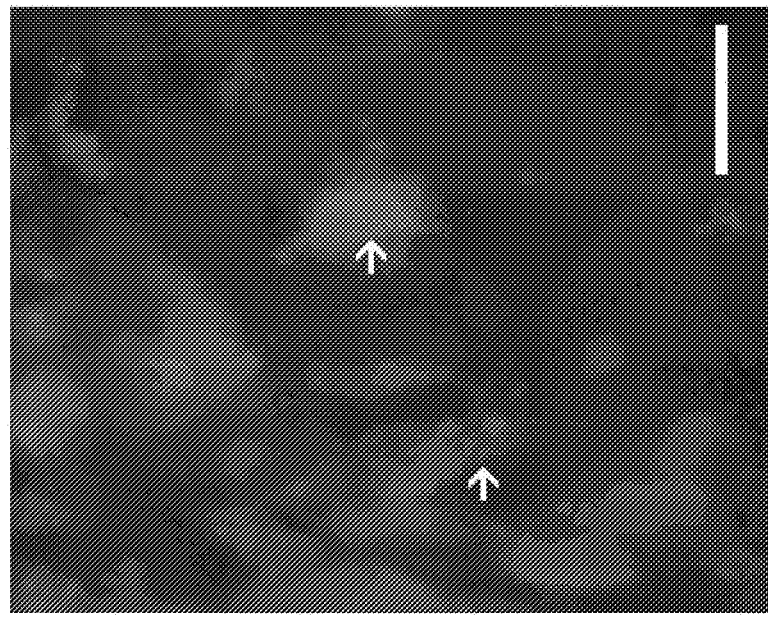
FIG. 3A illustrates microscopic imaging of TGF-β positive fibroblast-like cells and DAPI nuclear staining, according to a specific example embodiment of the disclosure.
Figure 3C:
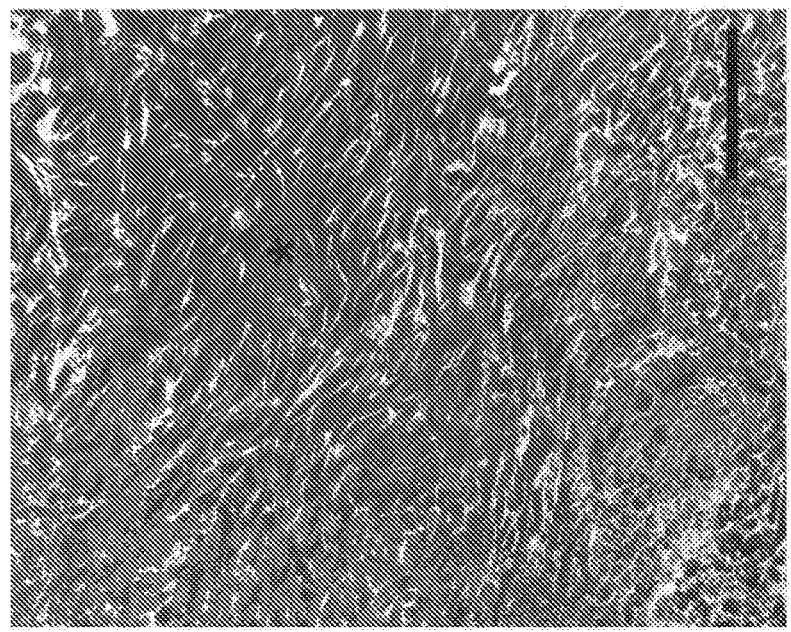
FIG. 3C illustrates microscopic imaging of tissue collected from the G3 treatment group having fibroblast-like cells with scarce collagen fibers, according to a specific example embodiment of the disclosure.
Figure 3B:
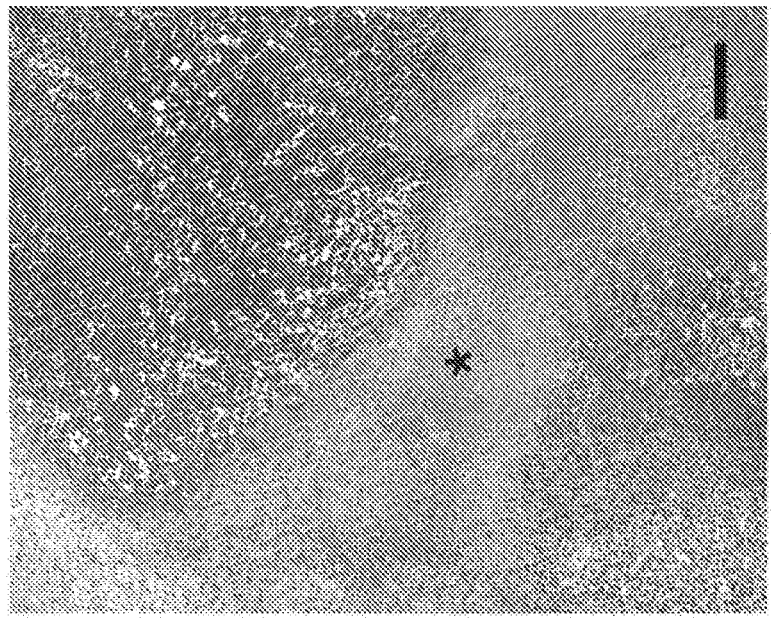
FIG. 3B illustrates microscopic imaging of tissue collected from the G1 treatment group and stained with H&E, according to a specific example embodiment of the disclosure.
Figure 3E:
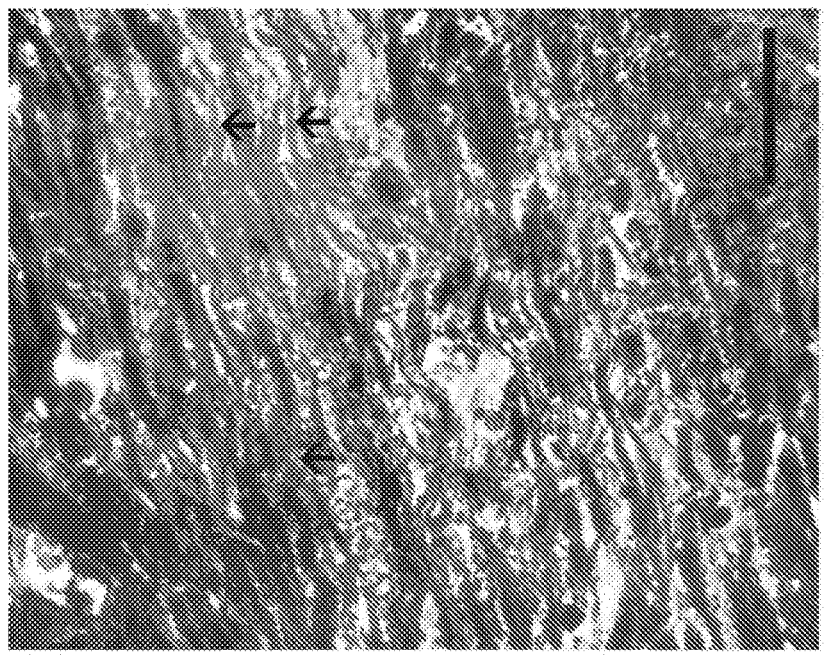
FIG. 3E illustrates microscopic imaging of tissue collected from the G4 treatment group and stained with Gomori's trichome.
Figure 3D:
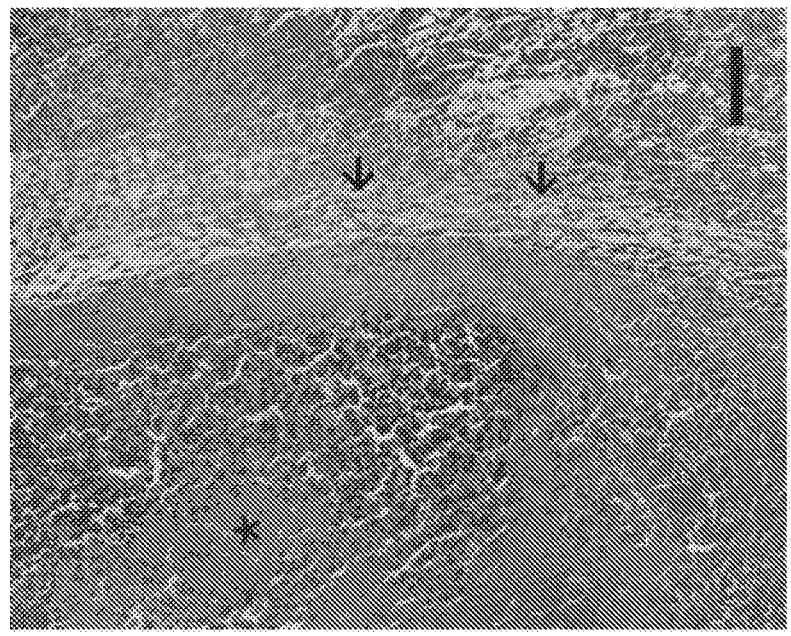
FIG. 3D illustrates microscopic imaging of tissue collected from the G4 treatment group showing collagen organization, according to a specific example embodiment of the disclosure.

FIG. 3A illustrates TGF-β positive fibroblast-like cells (green staining indicated by arrows) and DAPI nuclear staining (blue). TGF-β positive cells were primarily detected in the G3 and G4 treatment groups. The bar represents 10 μm. Color renderings of FIG. 3A illustrate predominantly blue DAPI nuclear staining with a minority of the image showing the green staining of TGF-β positive fibroblast-like cells.

The collagen fibers in treatment groups G1 and G3 were poorly organized, as illustrated in FIGS. 3B and 3C. FIG. 3B illustrates poorly organized collagen fibers in tissue collected from the G1 treatment group as shown by the absence of a delimited border surrounding the necrotic zone (indicated by an asterisk). The bar represents 50 m. FIG. 3C illustrates tissue collected from the G3 treatment group having fibroblast-like cells with scarce collagen fibers (as indicated by an asterisk). The bar represents 20 μm.

As illustrated in FIG. 3D, the collagen in the G4 treatment group was more organized and developed than that found in the G2 treatment group with connective tissue sheaths (indicated by arrows) and surrounding necrotic zones (indicated by asterisks). The bar represents 50 m. FIG. 3E illustrates the presence of abundant collagen fibers in a tissue sample collected from the G4 treatment group. The bar represents 20 m.

Figure 4B:
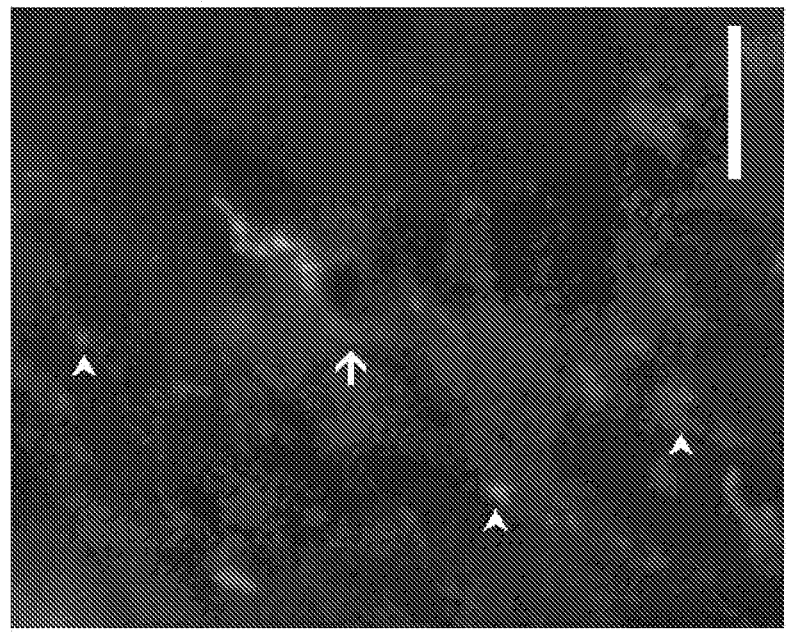
FIG. 4B illustrates microscopic imaging of tissue collected from the G2 or G4 treatment groups and stained with acridine orange—auramine O, according to a specific example embodiment of the disclosure.
Figure 4A:
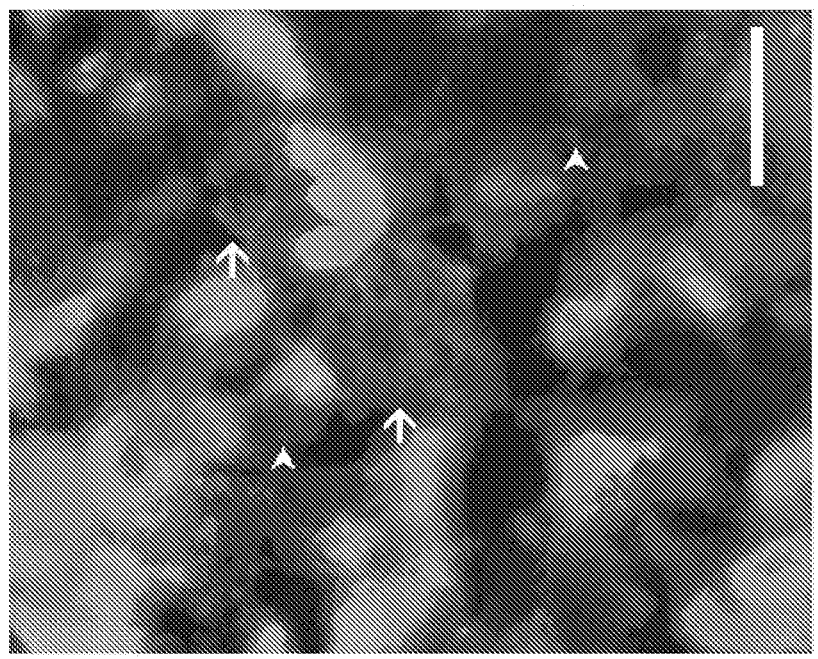
FIG. 4A illustrates microscopic imaging of tissue collected from the G3 treatment group and stained with acridine orange—auramine O, according to a specific example embodiment of the disclosure.

Tumor slides were stained with acridine orange-auramine O as described in EXAMPLE 7, to detect the presence of BCG bacilli in the tumor tissue. Findings indicated that BCG bacilli localization to the tumor tissue is dependent on the presence of formalin. BCG bacilli were detected in the tumoral stroma of the G2, G3, and G4 treatment groups, but not in the G1 control group. Moreover, in the G3 treatment group (i.e., without formalin) BCG was located inside the phagocytes thereby demonstrating the invasive capacity of the live mycobacteria (FIG. 4A). By contrast, in the G2 and G4 treatment groups the BCG mycobacteria (attenuated by the formalin) were located in the extracellular spaces (indicated by arrows) (FIG. 4B). The scale bars for FIGS. 4A and 4B is 10 μm.

Figure 5B:
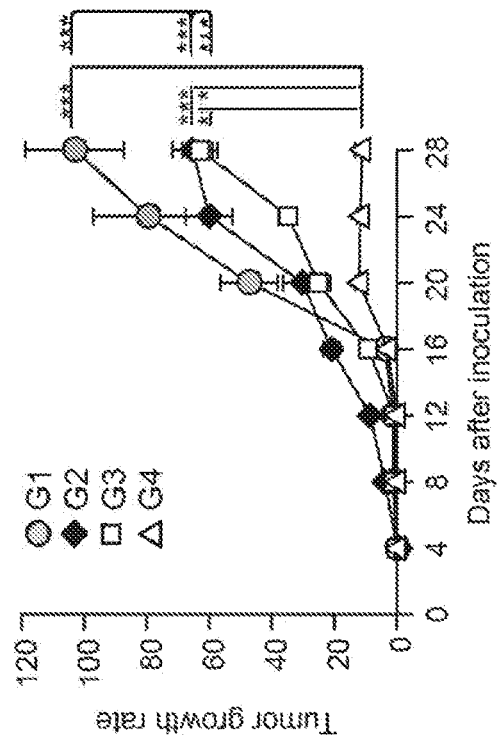
FIG. 5B is a graph illustrating tumor growth rate calculated as a percentage of volume increase with respect to the initial volume, according to a specific example embodiment of the disclosure.
Figure 5A:
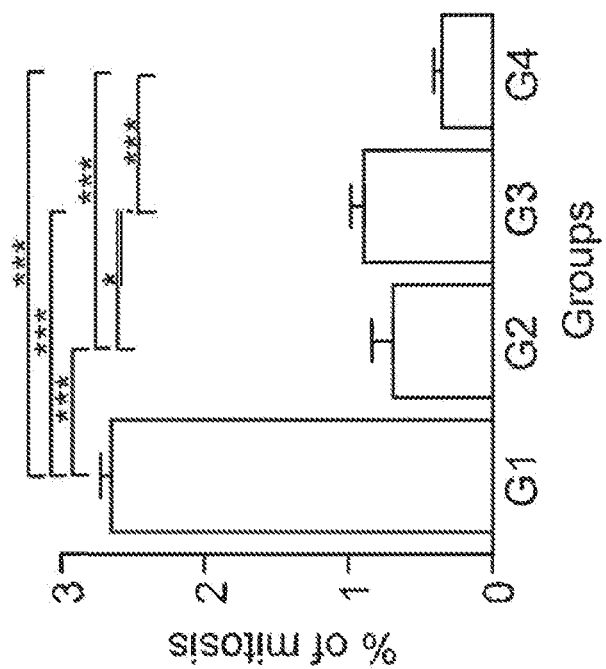
FIG. 5A is a bar graph illustrating the percent of mitosis observed in the G1, G2, G3, and G4 treatment groups, according to a specific example embodiment of the disclosure.
Figure 5D:
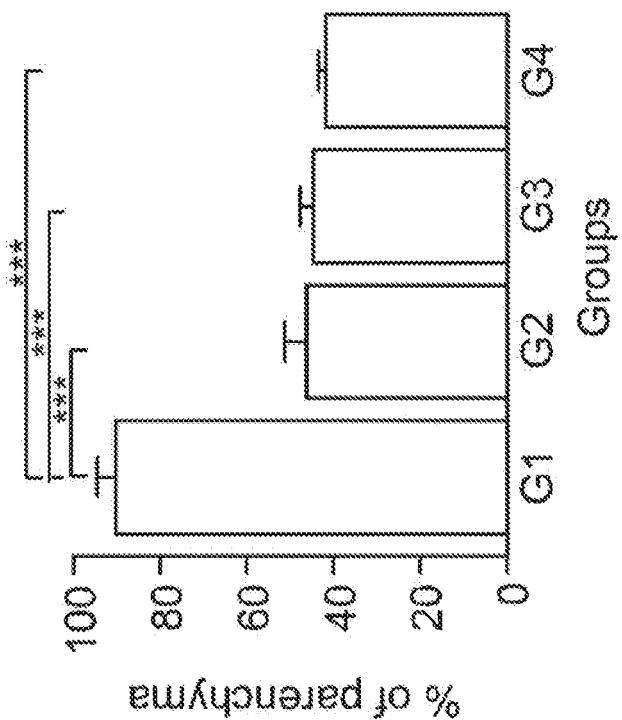
FIG. 5D is a bar graph illustrating the percent of tumor parenchyma present in the G1, G2, G3, and G4 treatment tissue samples, according to a specific example embodiment of the disclosure.
Figure 5C:
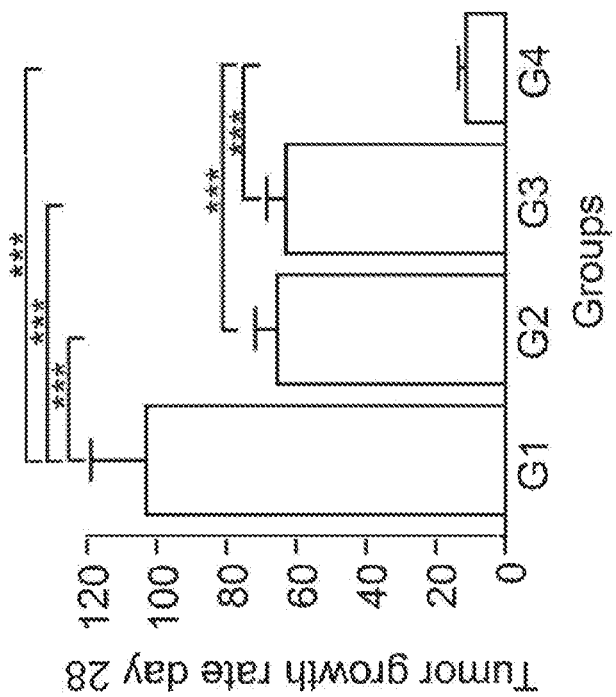
FIG. 5C is a bar graph illustrating tumor growth rate at 28 days post-inoculation, according to a specific example embodiment of the disclosure.
Figure 5E:
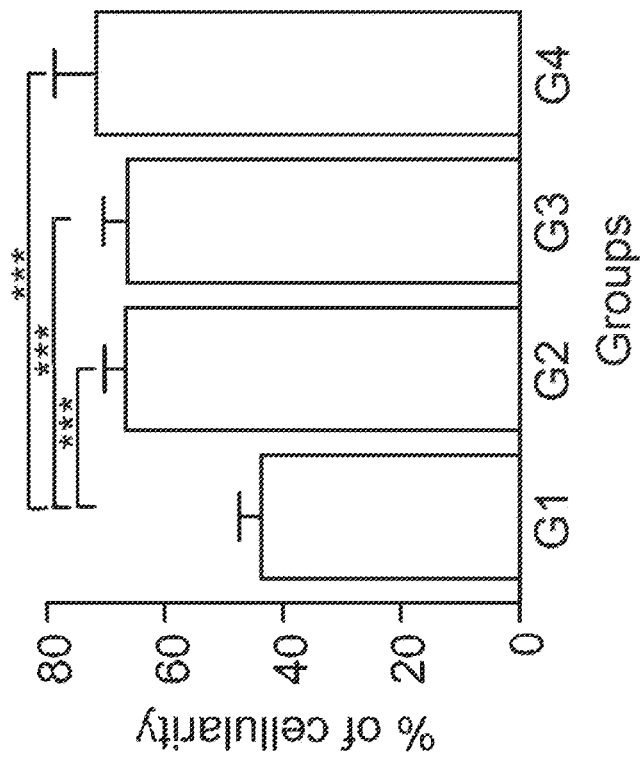
FIG. 5E is a bar graph illustrating the percent of cellularity observed in the G1, G2, G3, and G4 treatment tissue samples, according to a specific example embodiment of the disclosure.

Example 9: Results of Treatment of Mouse Breast Cancer Subjects-Statistical Analysis An effective antitumor therapy should arrest tumor cell proliferation. Tumor slides were stained with H&E, as described in EXAMPLE 7, and analyzed for mitosis rates. FIG. 5A is a bar graph illustrating the percent of mitosis observed in the G1, G2, G3, and G4 treatment groups. FIG. 5B is a graph illustrating tumor growth rate calculated as a percentage of volume increase with respect to the initial volume (G1 indicated as grey circles, G2 indicated as black diamonds, G3 indicated as open squares, and G4 indicated as open triangles). FIG. 5C is a bar graph illustrating tumor growth rate at 28 days post-inoculation. FIG. 5D is a bar graph illustrating the percent of tumor parenchyma present in the G1, G2, G3, and G4 treatment tissue samples. FIG. 5E is a bar graph illustrating the percent of cellularity observed in the G1, G2, G3, and G4 treatment tissue samples. The data in FIGS. 5A, 5B, 5C, 5D, AND 5E is shown as the mean±SEM of five mice per group (*, P≤0.05; , P≤0.01; *, P≤0.001).

G4 had the lowest mitosis percentage (FIG. 5A) and the lowest tumor growth rate (FIG. 5B AND FIG. 5C), demonstrated by an 11-fold net volume increase versus a 102-fold volume increase in the G1 treatment group (p≤0.05). Thus, the G4 treatment group (i.e., the vaccine) had the best performance arresting the tumor proliferation. The G2, G3, and G4 treatment groups showed diminishment of tumor parenchyma with respect to G1 (p≤0.05) (FIG. 5D). A high mitosis and parenchyma percentages in the G1 treatment group, may indicate that the high tumor growth rate is due to tumor cell proliferation, not by leukocyte infiltration. The cellularity in G2, G3, and G4 treatment groups, increased compared to G1 control group (p≤0.05) (FIG. 5E). Despite similar necrosis and cellularity percentages, the G2 and G3 treatment groups presented tumor growth rates higher than the G4 treatment group. This may indicate the presence of immunosuppressive conditions, which are impeding an effective tumor elimination.

The activation of dendritic cells is essential for the generation of an effective antitumor response. These cells, in great quantity, exert protumoral and anti-inflammatory effects. Tumor slides were processed by immunohistochemistry to determine CD209, CD19, CD4, CD8, CD49b and IFN-γ positive cells percentage and stained with H&E for neutrophils quantification, as described in EXAMPLE 7.

The CD209+/T cell, CD8+/CD19+ and CD4+/CD8+ratios were calculated for each of the treatment groups.

Figure 6A:
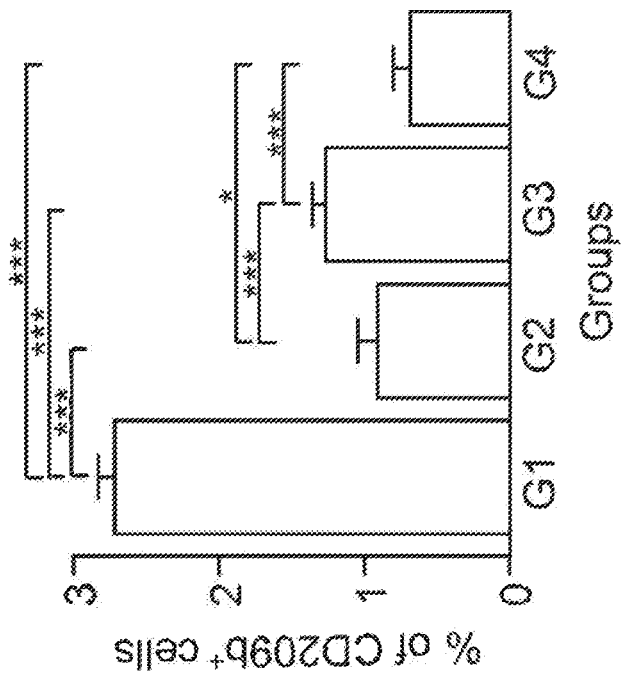
FIG. 6A is a bar graph illustrating the percent of CD209b+ cells present in the respective tissue samples, according to a specific example embodiment of the disclosure.

FIG. 6A is a bar graph illustrating the percent of CD209b+ cells (Antigen Present Cells (APCs)) present in the respective tissue samples. The data is shown as the mean±SEM of five mice per group (*, P≤0.05; , P≤0.01; *, P≤0.001). The G2, G3, and G4 treatment groups showed a significant diminution of CD209+cells relative to to the G1 control group (P≤0.001). Correlations between APCs with cellularity (p≤0.05, R=−0.93318) and tumor growth rate (p≤0.05, R=0.88105), indicates an immunosuppressive role.

Figure 6C:
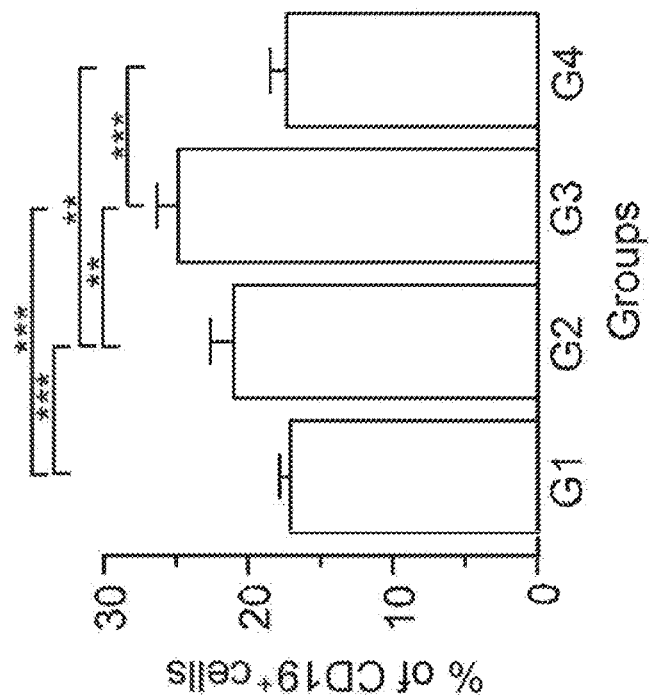
FIG. 6C is a bar graph illustrating the percent of B cells in the respective tissue samples, according to a specific example embodiment of the disclosure.
Figure 6B:
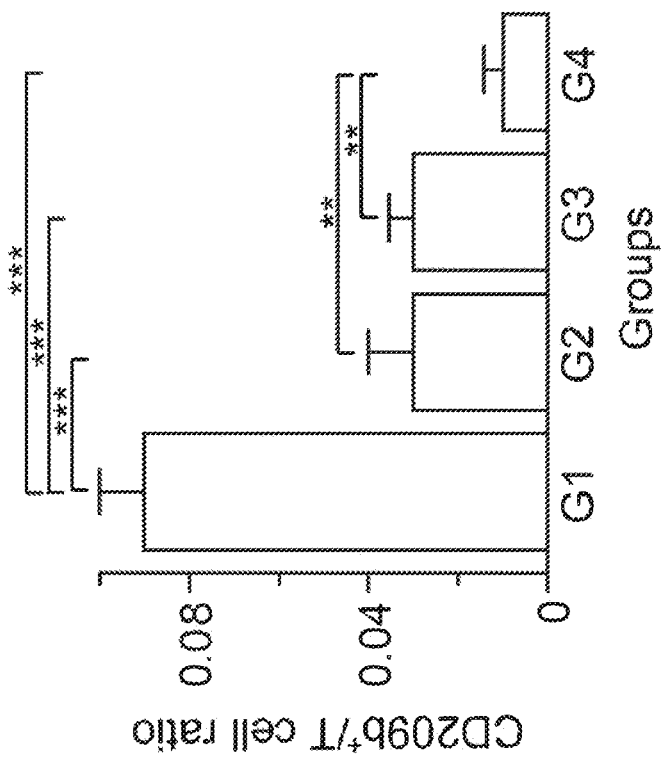
FIG. 6B is a bar graph illustrating the ratio of CD209b+ cells to T cells present in the respective tissue samples, according to a specific example embodiment of the disclosure.

FIG. 6B is a bar graph illustrating the ratio of CD209b+ cells (Antigen Present Cells (APCs)) to T cells present in the respective tissue samples. The data is shown as the mean±SEM of five mice per group (*, P≤0.05; , P≤0.01; *, P≤0.001). The APC/T cell ratio is an indicator of an effective priming of T CD8+ and T CD4+cells by APCs. Low APC/T cell ratio indicates a greater expansion of effector T CD8+ and CD4+cells, while high APC/T cell ratio suggests and inhibition of T cell activation that leads to immunosuppression. As shown in FIG. 6B, the G1 treatment group presented the highest APC/T cell ratio, followed by G2 and G3 with the same value. However, a positive correlation with mitosis percentage (p≤0.05, R=0.879) in the G2 treatment group indicates that the treatment was insufficient to activate dendritic cells. The G4 treatment group had the lowest APC/T cell ratio indicating an effective T cell activation by APCs (FIG. 6B).

In response to an effective immunotherapy, CD19+cells (B cells) can be differentiated in plasma cells that produce antibodies against the tumor. However, a subset of B cells, Bregs, can have protumoral effects. FIG. 6C is a bar graph illustrating the percent of B cells in the respective tissue samples. The data is shown as the mean±SEM of five mice per group (*, P≤0.05; , P≤0.01; *, P≤0.001). As shown in FIG. 6C the percent of B cells increased from the G1 treatment group to the G2 and G3 treatment groups, while the G4 treatment group had B cell levels similar to those seen in the G1 group (p≥0.05).

Figure 6E:
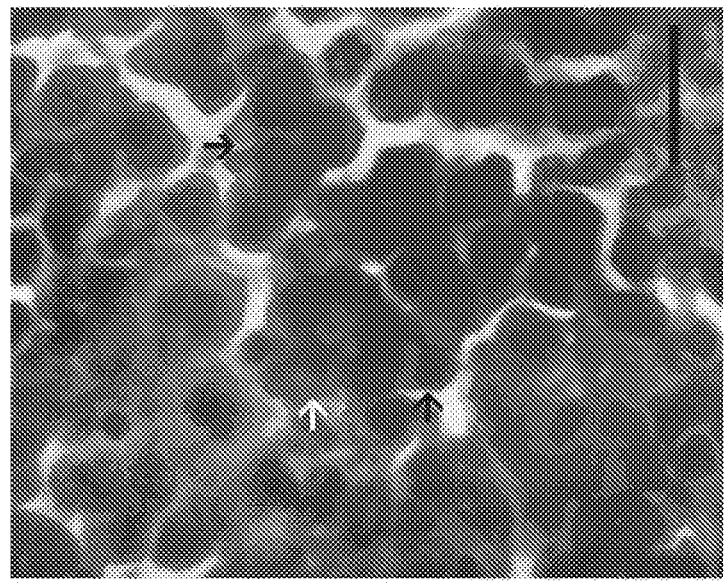
FIG. 6E is a microscope image of plasma cell infiltration in the G4 treatment group, according to a specific example embodiment of the disclosure
Figure 6D:
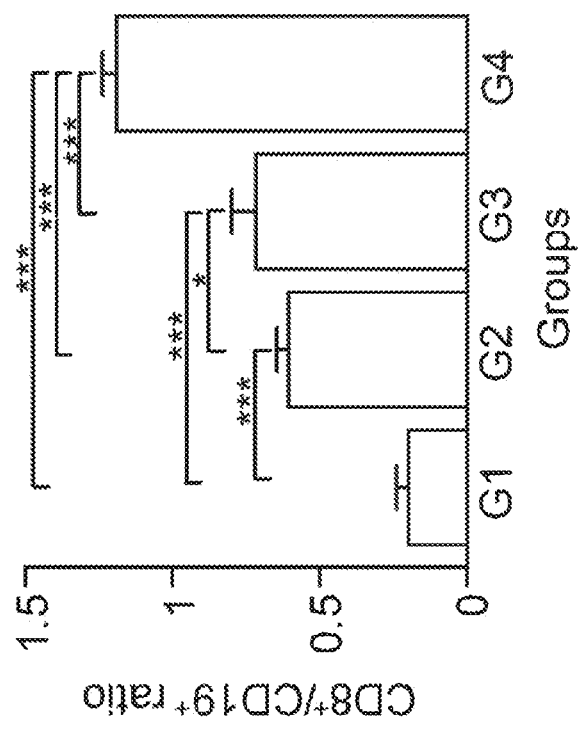
FIG. 6D is a bar graph illustrating the ratio of CD8+ T cells (CTL) to B cells, according to a specific example embodiment of the disclosure.

FIG. 6D is a bar graph illustrating the ratio of CD8+ T cells (CTL) to B cells. The data is shown as the mean±SEM of five mice per group (*, P≤0.05; , P≤0.01; *, P≤0.001). At high CTL/B cell ratios, the Breg level is low, suggesting a T CD8+cells stimulation by effector B cells. Low CTL/B cell ratios indicate Breg preponderance. As shown in FIG. 6D, treatment group G1 showed the lowest CTL/B cell ratio, followed by G2, G3, and G4. The ratio of CTL/B cells in the G4 treatment group was 10-fold higher than that seen in the G1 control group (p≤0.05). Additionally, the G1 treatment group had a positive correlation between CD19+ and CD209b+ cells (p≤0.05, R=0.919), indicating Breg recruitment by dendritic cells. In the G2 treatment group correlations between B cells and percentages of T CD4+(p≤0.05, R=0.96082) and T CD8+ cells (p≤0.05, R=0.95029) suggest T cells priming by B cells.

FIG. 6E is an image of plasma cell infiltration (indicated by arrows) in the G4 treatment group. The scale bar is 15 μm. The presence of plasma cells was seen in both the G3 and G4 treatment group samples and demonstrated the existence of antibody-secretor cells; however, the plasma cell infiltration was more abundant in the G4 treatment group. Accordingly, the data indicated that the G1 treatment group had a predominance of Bregs cells; the G2 and G3 treatment groups had a mixture of Bregs cells and effector B cells; and the G4 treatment group had primarily effector B cells resulting in the establishment of immune memory.

Figure 6G:
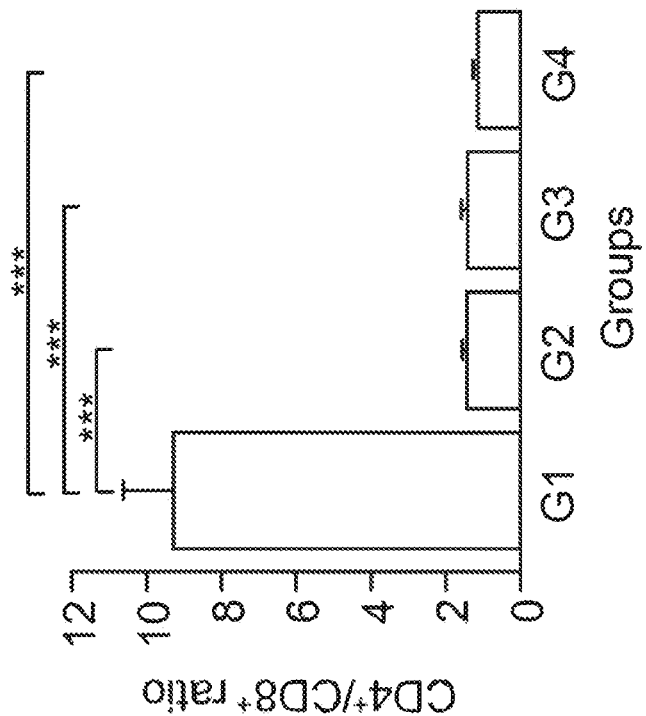
FIG. 6G is a bar chart illustrating the ratio of CD4/CD8 cells, according to a specific example embodiment of the disclosure.
Figure 6F:
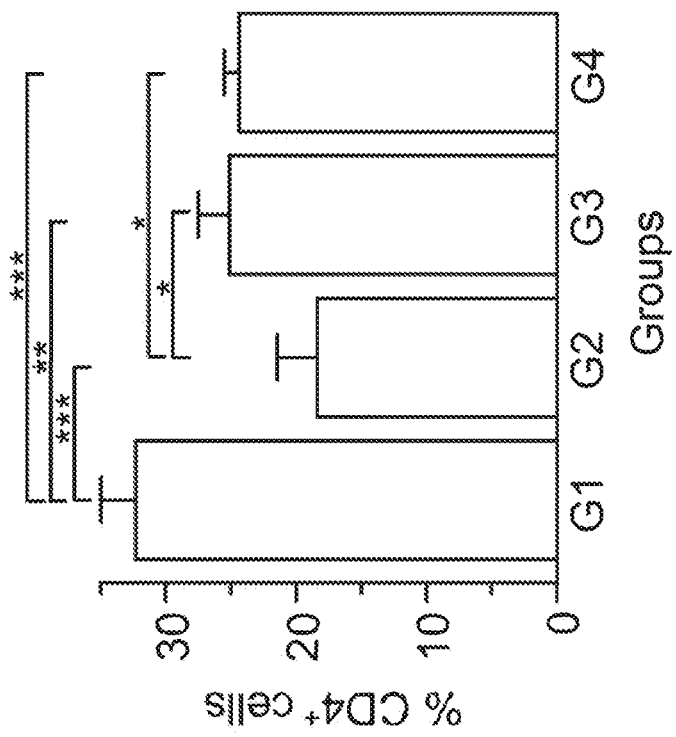
FIG. 6F is a bar graph illustrating the percentage of T CD4+ cells in the respective G1, G2, G3, and G4 treatment group tissue samples, according to a specific example embodiment of the disclosure.

FIG. 6F is a bar graph illustrating the percentage of T CD4+cells in the respective G1, G2, G3, and G4 treatment group tissue samples. The data is shown as the mean±SEM of five mice per group (*, P≤0.05; , P≤0.01; *, P≤0.001). T CD4+(CD4) and T CD8+(CD8) cells play essential roles in anti-tumor response. T CD4+cells have two main subsets: anti-tumor Th1 and anti-inflammatory Tregs. As shown in FIG. 6F, the G1 treatment group had the highest T CD4+cell count, while the G2 treatment group showed the lowest T CD4+cell count, followed by the G4 and G3 treatment groups respectively.

FIG. 6G is a bar chart illustrating the ratio of CD4/CD8 cells (to determine the prevalence of the type of T CD4+cells present). The data is shown as the mean±SEM of five mice per group (*, P≤0.05; , P≤0.01; *, P≤0.001). A low CD4/CD8 cell ratio indicates a predominance of T CD8+ and T CD4+Th1 cells with anti-tumor effect, and a minimal percentage of Tregs. A high CD4/CD8 cell ratio suggests a high proportion of Tregs. As shown in FIG. 6G, the G1 treatment group had the highest CD4/CD8 cell ratio while each of the G2, G3, and G4 treatment groups showed a marked reduction in its CD4/CD8 cell ratio relative to the G1 group. In the G2 treatment group, the percentage of T CD4+cells was correlated with mitosis percentage (p≤0.05, R=0.88497), tumor growth rate (p≤0.05, R=0.96694) and IFN-γ+cells (p≤0.05, R=−0.90981), suggesting a prevalence of Tregs cells. A low number of remaining Tregs in the G3 treatment group may be counteracted by IFN-γ, as indicated by a negative correlation between T CD4+ and IFN-γ+cells (p≤0.05, R=−0.97301).

Figure 6I:
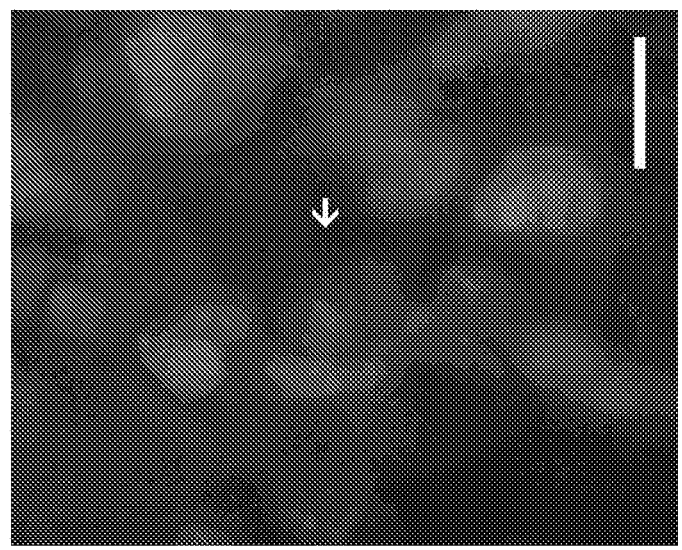
FIG. 6I is an image of DAPI nuclear stained G4 treatment cells showing CD8+ lymphocytes located close to tumor cells, according to a specific example embodiment of the disclosure.
Figure 6H:
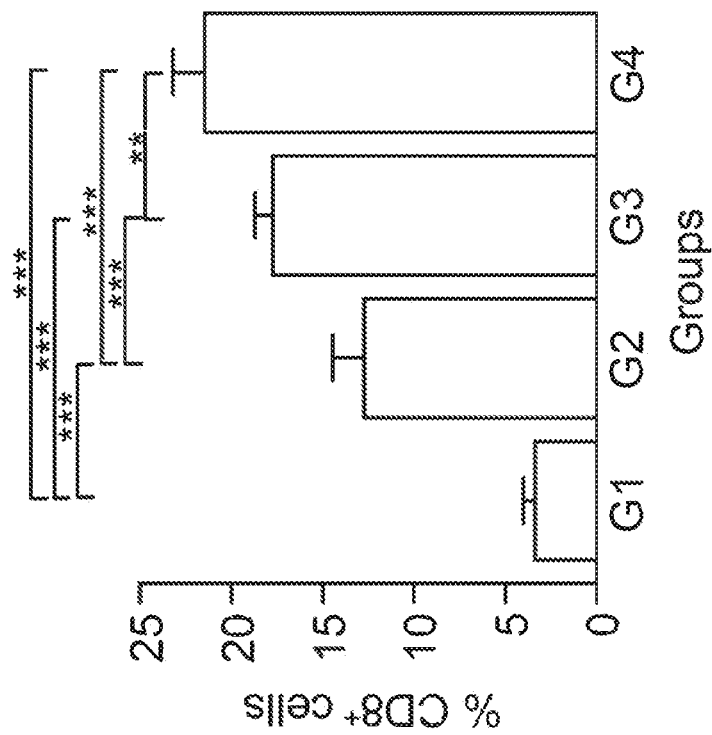
FIG. 6H is a bar graph indicating the percentage of CD8+ cells in the respective G1, G2, G3, and G4 treatment group tissue samples, according to a specific example embodiment of the disclosure.

FIG. 6H is a bar graph indicating the percentage of CD8+cells in the respective G1, G2, G3, and G4 treatment group tissue samples. The data is shown as the mean±SEM of five mice per group (*, P≤0.05; , P≤0.01; *, P≤0.001). The G4 treatment group showed an increased percentage of T CD8+cells followed by the G3, G2 and G1 treatment groups (FIG. 6H).

FIG. 6I is an image of DAPI nuclear stained (blue) G4 treatment cells showing CD8+lymphocytes (stained red) located close to tumor cells (arrow). The scale bar is 10 m. Lymphocytes were observed close to tumor cells primarily in the Z1 region indicating cytolytic activity mediated by T CD8+cells. Because the G4 treatment cells had the highest T CD8+cell percentage and the lowest CD4/CD8 ratio this indicates that the T CD4+cells in this group are likely Th1 cells (i.e., having an anti-tumor effect).

Figure 6K:
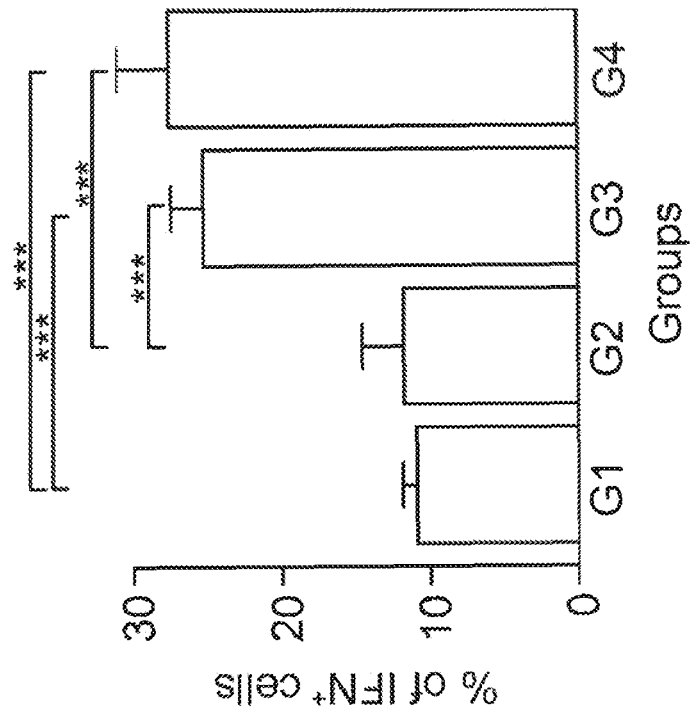
FIG. 6K is a bar graph indicating the percentage of IFN-γ+ in the respective G1, G2, G3, and G4 treatment group tissue samples, according to a specific example embodiment of the disclosure.
Figure 6J:
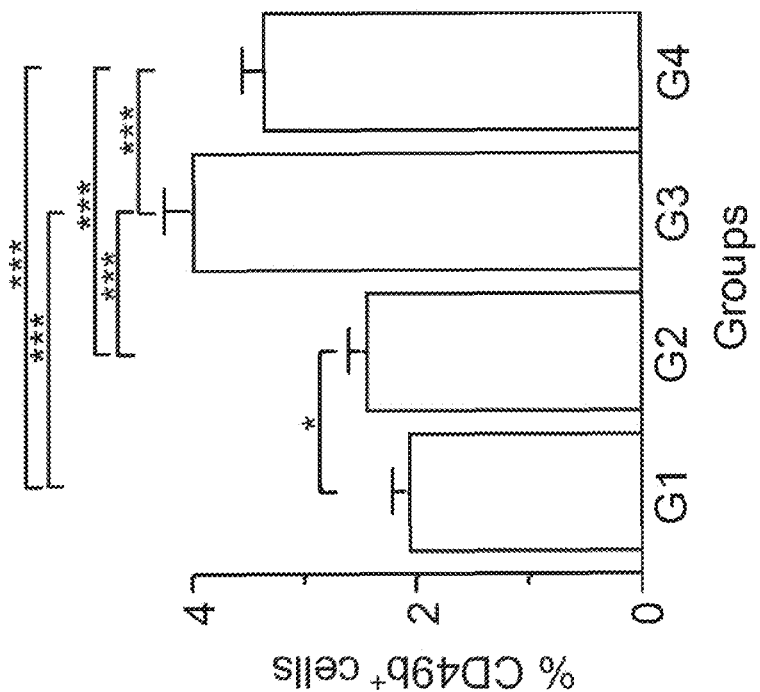
FIG. 6J is a bar graph indicating the percentage of CD49b+ cells in the respective G1, G2, G3, and G4 treatment group tissue samples, according to a specific example embodiment of the disclosure.

FIG. 6J is a bar graph indicating the percentage of CD49b+ cells (NK cells) in the respective G1, G2, G3, and G4 treatment group tissue samples. The data is shown as the mean±SEM of five mice per group (*, P≤0.05; , P≤0.01; *, P≤0.001). As shown in FIG. 6J, the G1 and G3 treatment groups presented the lowest and highest percentages of CD49+cells, respectively, whereas the G2 and G4 treatment groups showed intermediate values. This data indicates that the treatments including BCG had enhanced NK cell recruitment relative to those treatments without BCG. The G1 treatment group had a negative correlation between CD49b+ and T CD4+cells (p≤0.05, R=−0.91467), indicating that T CD4+cells may be inhibiting the proliferation or functions of NK cells. A possible activation of CD8+cells recruitment, mediated by IFN-γ secreted by NK cells, was present in G3 and G4, as indicated by the correlation (p≤0.05, G3: R=0.9244, G4: R=0.92186) between these cells.

FIG. 6K is a bar graph indicating the percentage of IFN-γ+ in the respective G1, G2, G3, and G4 treatment group tissue samples. The data is shown as the mean±SEM of five mice per group (*, P≤0.05; , P≤0.01; *, P≤0.001). IFN-γ+cells are a significant factor in tumor elimination. As shown in FIG. 6K, the G1 and G2 treatment groups had the lowest percentage of IFN-γ+cells, while the G3 and G4 treatment groups showed the highest percentage of IFN-γ+cells (p≥0.05). This pattern is consistent with the percentages of CD8+, CD4+ and NK cells across all treatment groups. The G3 and G4 treatment groups showed positive correlations between IFN-γ+ and CD49b+ cells (p≤0.05,G3: R=0.9244 G4: R=0.92186), suggesting that IFN-γ was mainly secreted by NK cells.

Figure 6M:
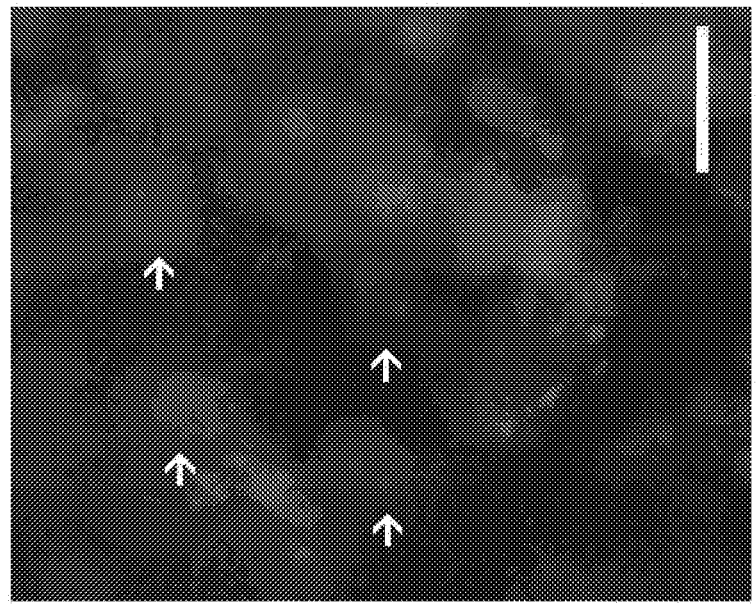
FIG. 6M is a microscope image of neutrophils from the G4 treatment group which tested positive for IFN-γ, according to a specific example embodiment of the disclosure.
Figure 6L:
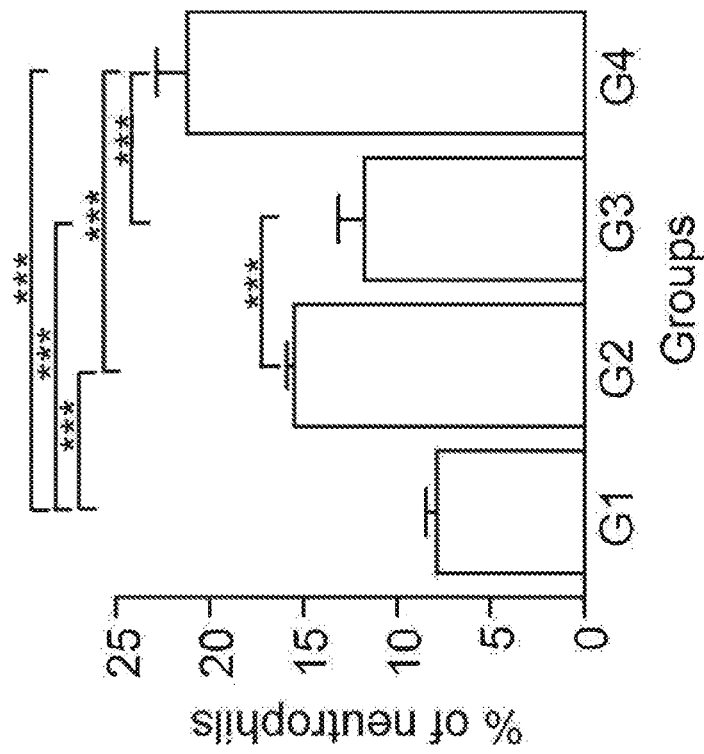
FIG. 6L is a bar graph indicating the percentage of neutrophils in the respective G1, G2, G3, and G4 treatment group tissue samples, according to a specific example embodiment of the disclosure.

FIG. 6L is a bar graph indicating the percentage of neutrophils in the respective G1, G2, G3, and G4 treatment group tissue samples. The data is shown as the mean±SEM of five mice per group (*, P≤0.05; , P≤0.01; *, P≤0.001). Neutrophils are associated with the initial stages of tumor necrosis. As illustrated in FIG. 6L, the G4 treatment group had the highest level of neutrophils followed by the G2, G3 and G1 treatment groups respectively.

FIG. 6M is a microscope image of neutrophils from the G4 treatment group which tested positive for IFN-γ. The bar represents 10 m. The correlation (p≤0.05, R=0.95522) between these variables in the G4 treatment group indicates that neutrophils may play an important role in tumor necrosis.

Tumor slides were processed by immunohistochemistry to determine the percentage of CD68+cells and Gr-1/CD11b+ cells, as described in EXAMPLE 7. An immunotherapy is considered successful if it prevents infiltration of pro-tumor cells, such as CD68+(tumor-associated macrophages (TAMs)) and Gr-1/CD11b+ cells (myeloid-derived suppressor cells (MDSCs)).

Figure 7B:
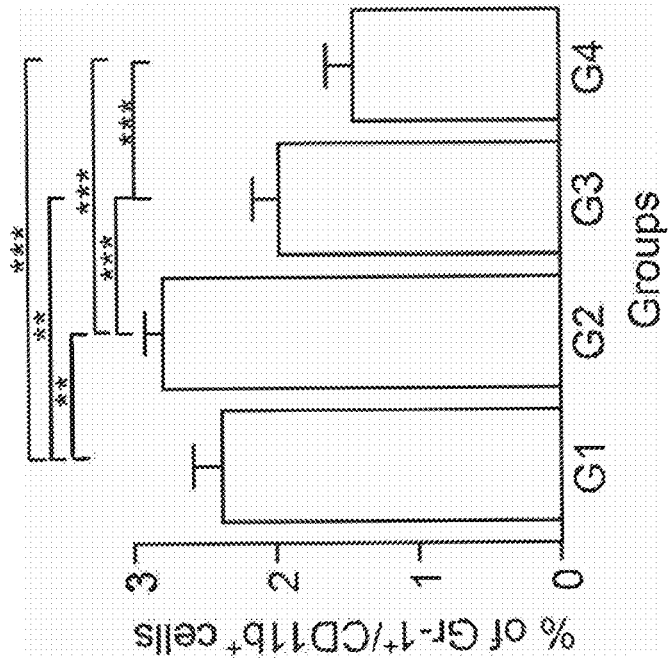
FIG. 7B is a bar graph indicating the percentage of Gr-1/CD1b+ cells in the respective G1, G2, G3, and G4 treatment group tissue samples, according to a specific example embodiment of the disclosure.
Figure 7A:
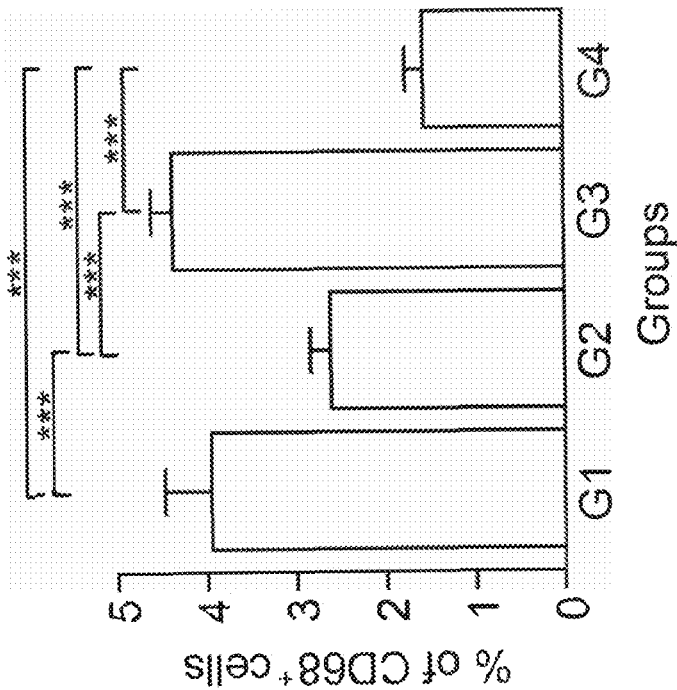
FIG. 7A is a bar graph indicating the percentage of CD68+ cells in the respective G1, G2, G3, and G4 treatment group tissue samples, according to a specific example embodiment of the disclosure.

FIG. 7A is a bar graph indicating the percentage of CD68+cells (TAMs) in the respective G1, G2, G3, and G4 treatment group tissue samples. The data is shown as the mean±SEM of five mice per group (*, P≤0.05; , P≤0.01; *, P≤0.001). As shown in FIG. 7A, the G3 treatment group had the highest percentage of TAMs, while the G4 treatment had the lowest. In the G1 treatment group, CD68+ cells were positively correlated with T CD4+cells (p≤0.05, R=0.9028), indicating that TAMs induce T CD4+cells differentiation toward Tregs. CD68+cells were negatively correlated with NK (p≤0.05, R=−0.93075) and IFN-γ+cells (p≤0.05, R=−0.90087) in the G1 treatment group, indicating an immunosuppressive role of TAMs. In contrast, the G2 treatment group showed a correlation between CD68+ and IFN-γ+cell percentages (p≤0.05, R=0.94345), suggesting the presence of macrophages with anti-tumoral properties. Supporting a pro-tumoral function of CD68+cells in the G3 treatment group, there are correlations between these cells and CD8+cells (p≤0.05, R=−0.98267), TGF-β concentration (p≤0.05, R=0.92955) and CD19+cells (p≤0.05, R=0.89642).

FIG. 7B is a bar graph indicating the percentage of Gr-1/CD11b+ cells (MDSCs) in the respective G1, G2, G3, and G4 treatment group tissue samples. The data is shown as the mean±SEM of five mice per group (*, P≤0.05; , P≤0.01; *, P≤0.001). The G2 treatment group had the highest percentage of MDSCs followed by the G1, G3, and G4 treatment groups respectively (FIG. 7B). A positive correlation was found in the G1 treatment group between MDSCs and TGF-β concentration (p≤0.05, R=0.93085), suggesting that MDSCs may secrete TGF-β. Additionally, a correlation between necrosis and MDSCs in the G2 treatment group (p≤0.05, R=0.92207) indicates that necrosis may stimulate MDSC recruitment. The diminishment of TAMs and MDSCs, considered tumor promoters, confirmed the high effectivity of the BCG/formalin/tumor cell homogenate vaccine (G4 treatment).

Tumor slides were processed by immunohistochemistry and stained with Gomori's trichome to determine TGF-β and collagen concentration, as described in EXAMPLE 7. FIG. 8A is a bar graph indicating the concentration of TGF-β in the respective G1, G2, G3, and G4 treatment group tissue samples. The data is shown as the mean±SEM of five mice per group (*, P≤0.05; , P≤0.01; *, P≤0.001). TGF-β is a cytokine with pro- and anti-tumoral roles, depending on tumor stage. As shown in FIG. 8A, the G4 treatment group had the highest TGF-β concentration, followed by the G2, G3 and G1 treatment groups respectively. The protumoral effects of TGF-β were demonstrated in the G1 treatment group by the correlations between this cytokine and the mitotic index (p≤0.05, R=0.96922), as well as with cellularity (p≤0.05, R=−0.93318). In the G3 treatment group cellularity (p≤0.05, R=−0.88177) correlated with TGF-β, supporting the same negative effects.

Figure 8B:
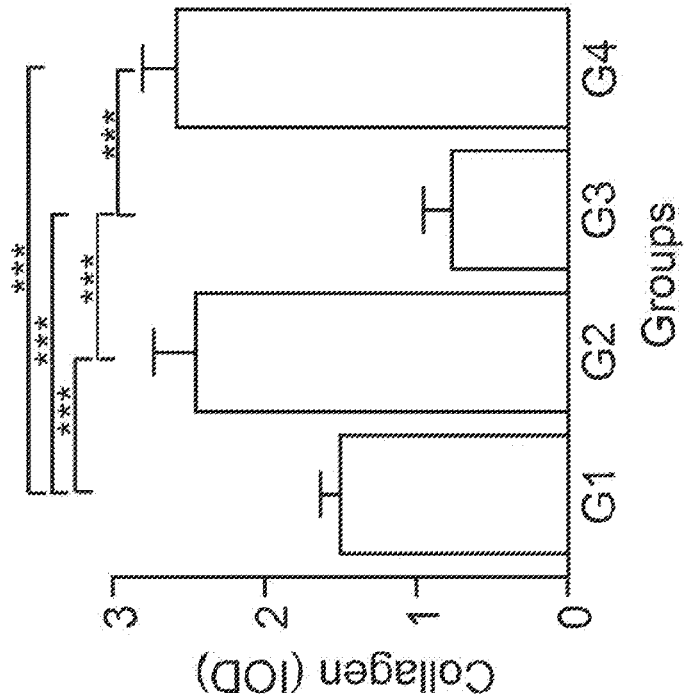
FIG. 8B is a bar graph indicating the concentration of collagen in the respective G1, G2, G3, and G4 treatment group tissue samples, according to a specific example embodiment of the disclosure.
Figure 8A:
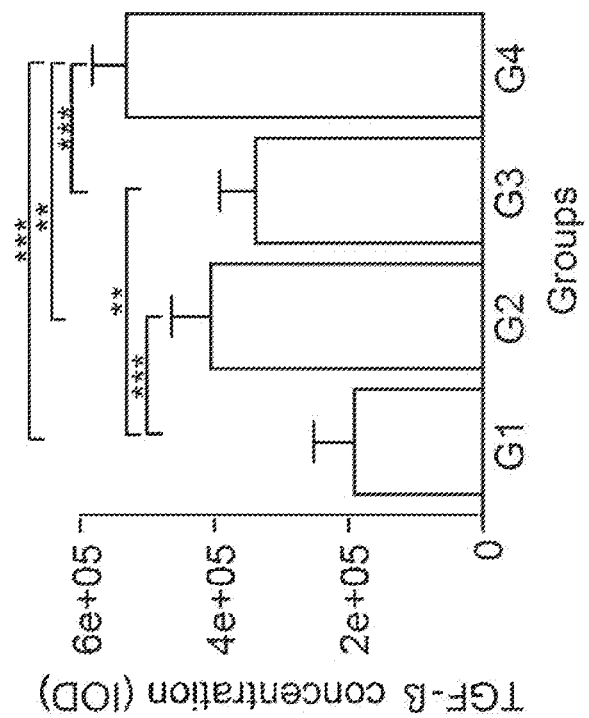
FIG. 8A is a bar graph indicating the concentration of TGF-β in the respective G1, G2, G3, and G4 treatment group tissue samples, according to a specific example embodiment of the disclosure.

FIG. 8B is a bar graph indicating the concentration of collagen in the respective G1, G2, G3, and G4 treatment group tissue samples. The data is shown as the mean±SEM of five mice per group (*, P≤0.05; , P≤0.01; *, P≤0.001). The highest collagen concentration was found in the G4 treatment group followed by the G2 treatment group, thereby showing the same trend with TGF-β concentration. The G1 and G3 treatment groups had the lowest collagen concentrations. High number of fibroblast and collagen concentration, in addition to all antitumoral evidence, indicate that in the G4 treatment group, TGF-β exerted tissue-healing, instead of promoting tumor progression.

What is claimed is:

1. A method of preparing an immunogenic composition operable as a treatment of cancer for a subject having a subject weight, the method comprising:
   homogenizing a tissue fragment in a suspension solution to form a cell homogenate,
      wherein the tissue fragment comprises neoplastic tissue from the subject or is autologous to neoplastic tissue from the subject;
   separating the cell homogenate to form a supernatant and a precipitate,
      wherein the supernatant comprises a protein composition comprising an immunoactive material;
   quantifying the protein composition;
   selecting a volume of the supernatant, based on the quantity of protein composition comprised in the supernatant, containing between about 6 mg to about 10 mg of the protein composition per kg of the subject weight; and
   mixing the volume of the supernatant with a BCG solution and a formaldehyde solution to generate the immunogenic composition, wherein the immunogenic composition has a final concentration comprising:
      about 6 mg to about 10 mg of the protein composition per kg of the subject weight,
      about 0.525 to about 0.725 mg of the BCG solution per mL of the immunogenic composition, and
      about 0.005% to about 0.035% of the formaldehyde solution per volume of the immunogenic composition.

2. The method of claim 1, wherein homogenizing the tissue fragment in the suspension solution is performed at a ratio of about 0.5 g of the tissue fragment per about 1 mL of the suspension solution.

3. The method of claim 1 further comprising:
harvesting a tumor tissue from the subject or from a tissue culture derived from a neoplastic breast tissue sample obtained from the subject to form a harvested tissue; and
fragmenting the harvested tissue to form the tissue fragment.

4. The method of claim 3 further comprising:
combining the tissue fragment with a storage solution; and
storing the tissue fragment at a temperature of ≤−80° C.

5. The method of claim 1 further comprising washing the tissue fragment in a wash solution of PBS and at least one antibiotic or antifungal.

6. The method of claim 1, wherein the suspension solution is PBS.

7. The method of claim 1 wherein homogenizing the tissue fragment includes pulverizing the tissue sample using at least 10 strokes of a glass homogenizer.

8. The method of claim 1, wherein separating the cell homogenate to form a supernatant and a precipitate comprises centrifugation.

9. The method of claim 8, wherein separating the cell homogenate to form a supernatant and a precipitate comprises centrifugation at a relative centrifugal force of 250 g for 10 minutes.

10. The method of claim 1, wherein quantifying the protein composition comprises performing a Bradford assay.

11. The method of claim 1, wherein the BCG solution comprises a live attenuated Danish strain 1331.

12. A method of preparing an immunogenic composition operable as a treatment of cancer for a subject having a subject weight, the method comprising:
homogenizing a tissue fragment in a suspension solution to form a cell homogenate,
wherein the tissue fragment comprises neoplastic tissue from the subject or is autologous to neoplastic tissue from the subject;
separating the cell homogenate to form a supernatant and a precipitate,
wherein the supernatant comprises a protein composition comprising an immunoactive material;
quantifying the protein composition;
selecting a volume of the supernatant, based on the quantity of protein composition comprised in the supernatant, containing between about 6 mg to about 10 mg of the protein composition per kg of the subject weight; and
mixing the volume of the supernatant with a BCG solution and a formaldehyde solution to generate the immunogenic composition, wherein the immunogenic composition has a final concentration comprising about 6 mg to about 10 mg of the protein composition per kg of the subject weight.

13. The method of claim 12, wherein homogenizing the tissue fragment in the suspension solution is performed at a ratio of about 0.5 g of the tissue fragment per about 1 mL of the suspension solution.

14. The method of claim 12 further comprising:
harvesting a tumor tissue from the subject or from a tissue culture derived from a neoplastic breast tissue sample obtained from the subject to form a harvested tissue; and
fragmenting the harvested tissue to form the tissue fragment.

15. The method of claim 14 further comprising:
combining the tissue fragment with a storage solution; and
storing the tissue fragment at a temperature of ≤−80° C.

16. The method of claim 12 further comprising washing the tissue fragment in a wash solution of PBS and at least one antibiotic or antifungal.

17. The method of claim 12, wherein the suspension solution is PBS.

18. The method of claim 12 wherein homogenizing the tissue fragment includes pulverizing the tissue sample using at least 10 strokes of a glass homogenizer.

19. The method of claim 12, wherein separating the cell homogenate to form a supernatant and a precipitate comprises centrifugation.

20. The method of claim 12, wherein the BCG solution comprises a live attenuated Danish strain 1331.

* * * * *